(12) United States Patent
Geva et al.

(10) Patent No.: US 11,529,506 B2
(45) Date of Patent: Dec. 20, 2022

(54) SYSTEM AND METHOD FOR ULTRASONIC BLADDER THERAPEUTIC AGENT DELIVERY

(71) Applicant: VENSICA MEDICAL LTD., Netanya (IL)

(72) Inventors: Avner Geva, Kfar Netter (IL); Giora Volpert, Pardes Hanna-Karkur (IL); Avraham Eftel, Tel Aviv (IL); Leonid Kushkuley, Rehovot (IL); Uri Shpolansky, Pardes Hanna-Karkur (IL)

(73) Assignee: VENSICA MEDICAL LTD., Netanya (IL)

( * ) Notice: Subject to any disclaimer, the term of this patent is extended or adjusted under 35 U.S.C. 154(b) by 0 days.

(21) Appl. No.: 17/044,184

(22) PCT Filed: Apr. 1, 2019

(86) PCT No.: PCT/IL2019/050378
§ 371 (c)(1),
(2) Date: Sep. 30, 2020

(87) PCT Pub. No.: WO2019/193591
PCT Pub. Date: Oct. 10, 2019

(65) Prior Publication Data
US 2021/0052873 A1 Feb. 25, 2021

Related U.S. Application Data

(60) Provisional application No. 62/651,194, filed on Apr. 1, 2018.

(51) Int. Cl.
*A61M 37/00* (2006.01)
*A61M 25/10* (2013.01)

(52) U.S. Cl.
CPC .... *A61M 37/0092* (2013.01); *A61M 25/1011* (2013.01); *A61M 2025/1093* (2013.01); *A61M 2210/1085* (2013.01)

(58) Field of Classification Search
CPC .......... A61M 37/0092; A61M 25/1011; A61M 2025/1093; A61M 2210/1085;
(Continued)

(56) References Cited

U.S. PATENT DOCUMENTS 6,296,619 B1    10/2001   Brisker et al.
7,927,836 B2    4/2011    Doelle et al.
(Continued)

FOREIGN PATENT DOCUMENTS

WO    2014105754 A1    7/2014
WO    2015014487 A1    2/2015
(Continued)

OTHER PUBLICATIONS

PCT Search Report for International Application No. PCT/IL2019/050378, dated Jul. 2, 2019, 5 pp.
(Continued)

*Primary Examiner* — Bhisma Mehta
*Assistant Examiner* — Phoebe Anne Staton
(74) *Attorney, Agent, or Firm* — The Roy Gross Law Firm, LLC; Roy Gross

(57) ABSTRACT

A catheter for ultrasonic-driven bladder therapeutic agent delivery, including: a tube having a proximal expandable portion and a distal end, and at least one transducer sleeve accommodating at least one ultrasound transducer mounted on the tube between the proximal expandable portion and the distal end.

15 Claims, 18 Drawing Sheets

(58) Field of Classification Search
CPC .......... A61M 2025/1052; A61M 31/00; A61M 2025/105; A61M 2025/1013; A61M 2025/1015; A61M 2025/1061; A61M 29/00; A61N 7/022; A61N 2007/0039; A61N 2007/0043

See application file for complete search history.

(56) References Cited

U.S. PATENT DOCUMENTS

| | | | |
|---|---|---|---|
| 9,937,245 B2 | 4/2018 | Pfeil et al. | |
| 2003/0092667 A1* | 5/2003 | Tachibana | A61K 41/0047 604/20 |
| 2005/0192560 A1* | 9/2005 | Walls | A61M 25/0017 264/478 |
| 2008/0086083 A1* | 4/2008 | Towler | A61M 25/1029 604/103.06 |
| 2013/0197555 A1 | 8/2013 | Schaer | |
| 2014/0058294 A1 | 2/2014 | Gross et al. | |
| 2015/0164401 A1 | 6/2015 | Toth et al. | |
| 2019/0117242 A1* | 4/2019 | Lawinger | A61B 18/26 |

FOREIGN PATENT DOCUMENTS

| | | |
|---|---|---|
| WO | 2016151595 A1 | 9/2016 |
| WO | 2017161331 A1 | 9/2017 |

OTHER PUBLICATIONS

PCT Written Opinion for International Application No. PCT/IL2019/050378, dated Jul. 2, 2019, 6 pp.
PCT Search Report for International Application No. PCT/IL2019/050378, dated Oct. 6, 2019, 7 pp.
Schurch et al., "Botulinum Toxin Type A Is a Safe and Effective Treatment For Neurogenic Urinary Incontinence Results of a Single Treatment, Randomized, Placebo Controlled 6-Month Study" The Journal of Urology vol. 174, pp. 196-200, (2005).

* cited by examiner

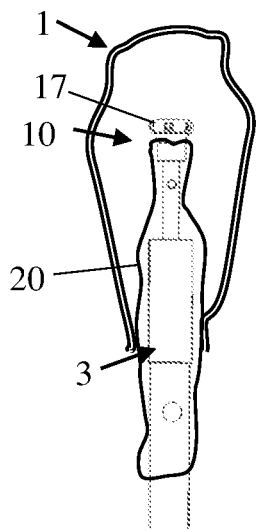
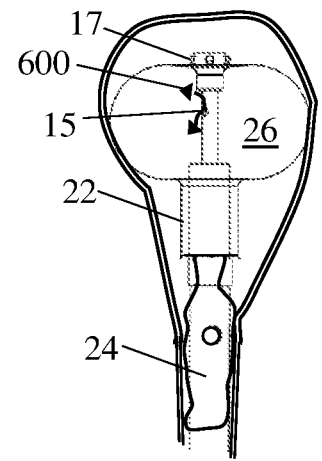
FIG 6A  FIG 6B
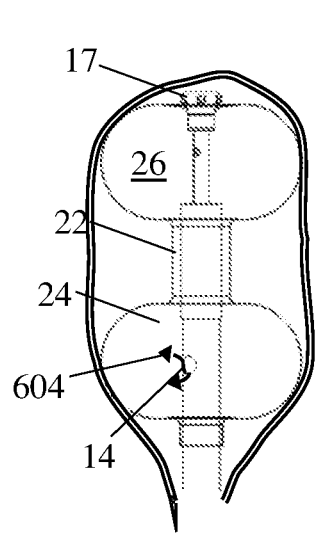
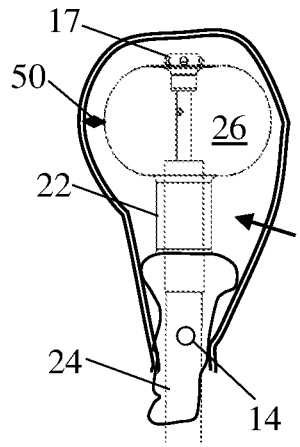
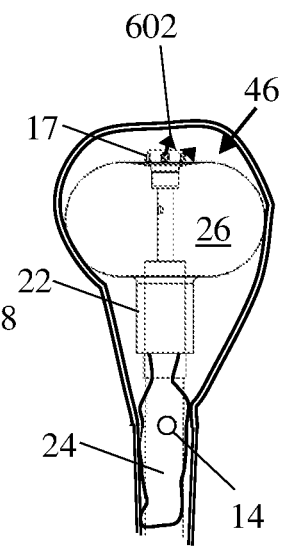
FIG 6E  FIG 6D
FIG 6C

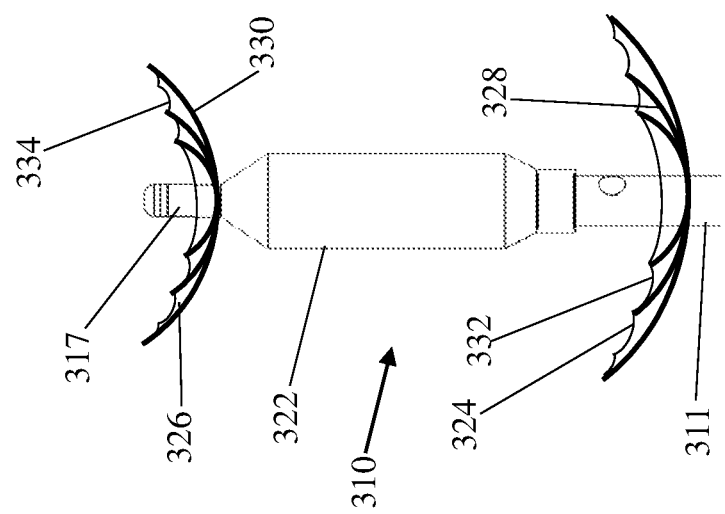
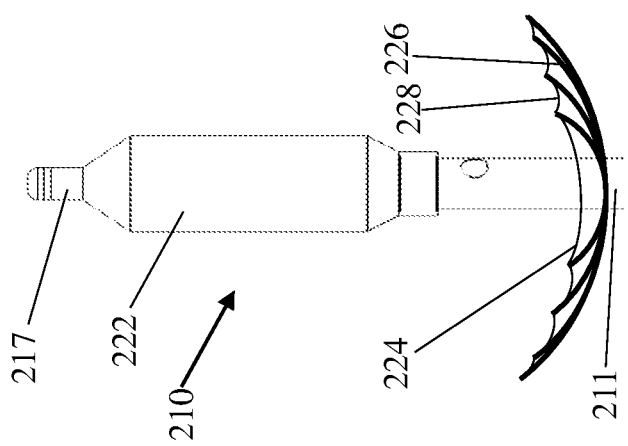

| Parameter | Power (W) | Burst ON (ms) | Burst OFF (ms) | Duty cycle (%) | Frequency (kHz) | Treatment time (min) | Incubation time post treatment (min) |
|---|---|---|---|---|---|---|---|
| value | 150 | 300 | 1700 | 15 | 200 | 15 | 10 |

FIG 15

| Patient | Avg. Volume / Micturation | Avg. No. of Nocturnal Urinations | Avg. No. of Incontinence | OAB-q Total Score |
|---|---|---|---|---|
| 3002 | +22% | -60% | No change | -4.1% |
| 3004 | +27% | -10% | -62.5% | -38.6% |

FIG 17

SYSTEM AND METHOD FOR ULTRASONIC BLADDER THERAPEUTIC AGENT DELIVERY

CROSS REFERENCE TO RELATED APPLICATIONS

This application is a National Phase of PCT Patent Application No. PCT/IL2019/050378 having International filing date of Apr. 1, 2019 which claims the benefit of priority under 35 U.S.C. § 119(e) from U.S. Provisional Patent Application No. 62/651,194 filed on Apr. 1, 2018, entitled "SYSTEM AND METHOD FOR ULTRASONIC BLADDER THERAPEUTIC AGENT DELIVERY". The contents of the above applications are all incorporated by reference as if fully set forth herein in their entirety.

This application is related to U.S. patent application Ser. No. 15/561,733 filed on Sep. 26, 2017, entitled "ULTRASONIC URINARY BLADDER DRUG DELIVERY".

The contents of the above applications are incorporated by reference as if fully set forth herein in their entirety.

FIELD OF THE INVENTION

The present invention, in some embodiments thereof, relates to a catheter for bladder therapeutic agent delivery and, more particularly, but not exclusively, to an ultrasonic-driven bladder therapeutic agent delivery.

BACKGROUND

Intravesical therapy of the urinary bladder involves the bladder inner surface which is covered with transitional epithelium lining called urothelium, and glycosaminoglycans (GAG) units found on the urothelium. Both the urothelium and the GAG units may function as an important barrier to toxins and waste found in the urine, giving the bladder wall its low permeability characteristic. However, this compact and tight barrier may also restrict effective penetration of therapeutic agents delivered into the bladder during intravesical treatments. Some therapeutic molecules may not penetrate the bladder barrier at all.

Ultrasound cavitation is a mechanism by which acoustic waves can increase tissue permeability. Cavitation bubbles collapse on the tissues with high energy and open up pores in the tissues, which result in the increased permeability of the tissues to therapeutic agents.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

According to an aspect of some embodiments of the present invention there is provided a catheter for ultrasonic-driven bladder therapeutic agent delivery, the catheter includes: a tube, two or more expandable portions mounted on the tube, one or more ultrasound transducers mounted on the tube between the two or more expandable portions, and a transducer sleeve disposed between the two or more expandable portions and accommodating the one or more transducers. According to some embodiments the transducer sleeve and the expandable portions include a single balloon. In some embodiments, the expandable portion comprises a stent.

According to some embodiments the maximal cross-sectional area of the transducer sleeve at an expanded state is smaller than the maximal cross-sectional area of any one of the expandable portions at least at their greatest circumference. According to some embodiments of the invention at least one of the expandable portions is spheroid and at least one of the expandable portions and the tube are concentric. According to some embodiments of the invention at least one of the expandable portions and the transducer are concentric.

According to some embodiments of the invention the tube includes at least one fluid port located within a lumen of at least one of the expandable portions and/or at least one fluid port along its length that opens to a lumen of a bladder. The port is configured to supply fluid into the lumen of the bladder and/or evacuate fluid out of the bladder.

According to some embodiments of the invention the transducer is elevated from a surface of the tube so that to define a gap between the transducer and the surface of the tube. According to some embodiments of the invention the greatest circumference of the transducer sleeve is less than 50% of the greatest circumference of at least one expandable portion and/or the inflation pressure of the transducer sleeve is greater than the inflation pressure of the expandable portions. According to some embodiments of the invention the tube includes one or more conduits that supply therapeutic fluid via the port. According to some embodiments of the invention the tube includes one or more conduits that supply gassed fluid via the port. According to some embodiments of the invention the tube includes one or more conduits that supply fluid via the port.

According to some embodiments of the invention the transducer is configured to form cavitations in the gassed therapeutic fluid.

According to an aspect of some embodiments of the present invention there is provided a catheter for ultrasonic-driven bladder therapeutic agent delivery, the catheter includes a tube, having a proximal portion and a distal end, a proximal expandable portion mounted on the proximal portion of the tube, one or more transducers mounted on the tube between the proximal expandable portion and the distal end, and a transducer sleeve between the proximal expandable portion and the distal end accommodating the one or more transducers. In some embodiments, one or more of the expandable portions comprises a balloon.

According to some embodiments of the invention the balloon is toroidal and/or configured to inflate distally towards the distal end. According to some embodiments of the invention the tube includes at least one fluid port along its length that opens to a lumen of a bladder and/or is located between the transducer and the balloon. According to some embodiments of the invention the port is configured to supply fluid into the lumen of the bladder and/or evacuate fluid out of the bladder.

According to some embodiments of the invention the greatest circumference of the transducer sleeve is less than 50% of the greatest circumference of the balloon. According to some embodiments a volume is defined between the transducers and the transducer sleeve. According to some embodiments the inflation pressure of the transducer sleeve is greater than the inflation pressure of the balloon. According to some embodiments of the invention the tube includes one or more conduits that supply therapeutic fluid via the port.

According to an aspect of some embodiments of the present invention there is provided a method for treating a bladder using a catheter for ultrasonic-driven bladder therapeutic agent delivery including: inserting a distal expandable portion of the catheter into the bladder via a urethra, expanding the expandable portion, supplying therapeutic fluid into the bladder through at least one therapeutic fluid port in the catheter, advancing the catheter in the bladder and inserting a proximal expandable portion of the catheter into the bladder, expanding the proximal expandable portion and trapping the therapeutic fluid between the distal expandable portion and the proximal expandable portion, and applying ultrasound to form cavitation in the therapeutic fluid. In some embodiments, the method for treating a bladder using a catheter for ultrasonic-driven bladder therapeutic agent delivery comprises supplying of therapeutic fluid into the bladder through at least one therapeutic fluid port in the catheter after stopping to emit ultrasound energy.

According to some embodiments of the invention the method includes supplying the therapeutic fluid through a port between the expandable portions. According to some embodiments of the invention the therapeutic fluid is gaseous therapeutic fluid.

According to an aspect of some embodiments of the present invention there is provided a method for treating a bladder using a catheter for ultrasonic-driven bladder therapeutic agent delivery including: inserting a distal expandable portion of the catheter into the bladder via a urethra, expanding the expandable portion, supplying gassed fluid into the bladder through at least one fluid port in the catheter, emitting ultrasound energy and forming cavitations in the gassed fluid, draining the bladder content, supplying therapeutic fluid into the bladder through at least one therapeutic fluid port in the catheter, and emitting ultrasound energy and forming cavitations in the therapeutic fluid.

According to some embodiments of the present invention the method includes draining and flushing the bladder with saline prior to supplying the gassed fluid into the bladder.

According to some embodiments the method includes stopping emitting ultrasound energy during the draining of the bladder content and/or the supplying of the therapeutic fluid into the bladder through at least one therapeutic fluid port in the catheter.

According to an aspect of some embodiments of the present invention there is provided a catheter for ultrasonic-driven bladder therapeutic agent delivery, including: a tube having a proximal expandable portion and a distal end; and at least one transducer sleeve accommodating at least one ultrasound transducer mounted on the tube between the proximal expandable portion and the distal end.

According to an aspect of some embodiments of the present invention there is provided a catheter wherein at least one expandable portion is expandable inside a bladder from a contracted state to an expanded state at which the expandable portion is urged against the bladder wall to form a sealed volume within the bladder between the expandable portion and a trigone area of said bladder.

In some embodiments, the catheter includes at least one additional expandable portion, wherein the transducer sleeve is disposed between the proximal and said at least one additional expandable portion. In some embodiments, the transducer sleeve and at least one of the expandable portions are in fluid communication.

In some embodiments, the maximal cross-sectional area of the transducer sleeve at an expanded state is smaller than the maximal cross-sectional area of any one of the expandable portions at least at their greatest circumference. In some embodiments, at least one of the expandable portions is spheroid.

In some embodiments, at least one of the expandable portions and the tube are concentric. In some embodiments, at least one of the expandable portions and the transducer are concentric. In some embodiments, the tube comprises at least one fluid port located within a lumen of at least one of the expandable portions.

In some embodiments, the tube comprises at least two fluid ports in fluid communication with the lumen of the transducer sleeve and wherein fluid flow is maintained between the ports. In some embodiments, the transducer is positioned between the ports.

In some embodiments, the tube comprises at least one therapeutic fluid port along its length that opens to a lumen of a bladder. In some embodiments, the catheter includes a blind tip at the distal end, wherein the at least one therapeutic fluid port is positioned along the circumference of the tip. In some embodiments, the transducer is elevated from a surface of the tube so that to define a gap between the transducer and the surface of the tube.

In some embodiments, the catheter comprises at least one spacer positioned on the tube and wherein the transducer is mounted on the at least one spacer. In some embodiments, the greatest circumference of the transducer sleeve is less than 50% of the greatest circumference of at least one expandable portion. In some embodiments, the tube comprises one or more conduits that supply fluid via said therapeutic fluid port.

In some embodiments, at least one expandable portion is toroidal. In some embodiments, at least one expandable portion is configured to inflate distally towards the distal end. In some embodiments, the catheter comprises at least one fluid port located between the transducer and at least one expandable portion.

In some embodiments, an expanded state a volume is defined between the transducer and the transducer sleeve.

According to an aspect of some embodiments of the present invention there is provided a method for treating a bladder using a catheter for ultrasonic-driven bladder therapeutic agent delivery including: inserting a distal expandable portion of the catheter into the bladder via a urethra, expanding the expandable portion, supplying therapeutic fluid into the bladder through at least one therapeutic fluid port in the catheter, advancing the catheter in the bladder and inserting a proximal expandable portion of the catheter into the bladder, expanding the proximal expandable portion and trapping the therapeutic fluid between the distal expandable portion and the proximal expandable portion, and forming cavitations in the therapeutic fluid.

In some embodiments, the method includes supplying the therapeutic fluid through a port between the expandable portions. In some embodiments, the therapeutic fluid is gaseous therapeutic fluid.

According to an aspect of some embodiments of the present invention there is provided a method for treating a bladder using a catheter for ultrasonic-driven bladder therapeutic agent delivery including: inserting a distal expandable portion of the catheter into the bladder via a urethra, supplying fluid into the bladder through at least one fluid port in the catheter, emitting ultrasound energy and forming cavitations in the gassed fluid, draining the bladder content, and supplying therapeutic fluid into the bladder through at least one therapeutic fluid port in the catheter. In some embodiments, said fluid is gassed.

In some embodiments, the method includes expanding a distal expandable portion of the catheter prior to supplying therapeutic fluid into the bladder. In some embodiments, the method includes draining and flushing the bladder with saline prior to supplying the gassed fluid into the bladder.

In some embodiments, the method includes stopping emitting ultrasound energy during the draining of the bladder content and/or the supplying of the therapeutic fluid into the bladder through at least one therapeutic fluid port in the catheter. In some embodiments, the method includes further advancing a proximal expandable portion prior to emitting ultrasound energy. In some embodiments, the method includes expanding proximal expandable portion prior to emitting ultrasound energy.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 6A-6E are plan view simplified illustrations of a method of implementation of a catheter for ultrasonic-driven treatment of a bladder, in accordance with some embodiments of the invention;

FIG. 13 is a side view simplified illustration of a catheter for ultrasonic-driven bladder therapeutic agent delivery in accordance with some embodiments of the invention;

FIG. 14 is a side view simplified illustration of a catheter for ultrasonic-driven bladder therapeutic agent delivery in accordance with some embodiments of the invention;

FIG. 15 is an exemplary chart of parameters of implementation of a catheter for ultrasonic-driven treatment of a bladder, in accordance with some embodiments of the invention;

FIG. 17, which is a table of efficacy data from two human patients comparing pre-procedure bladder function to 14 days post procedure bladder function.

DETAILED DESCRIPTION

Figure 1A:
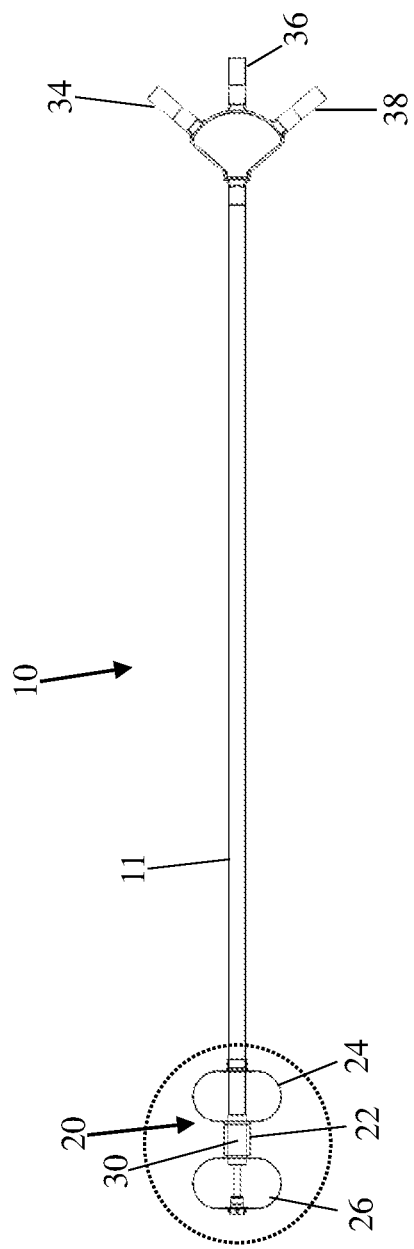
FIGS. 1A and 1B, collectively referred to as FIG. 1, are a plan view and perspective enlarged view of the encircled area of FIG. 1A, simplified illustrations of a catheter for ultrasonic-driven bladder therapeutic agent delivery in accordance with some embodiments of the invention.

Some of the challenges that exist in the ultrasound cavitation mechanism are in that cavitation may need to form in a fluid in proximity to the tissue surface to be treated to enhance therapeutic agent delivery. Moreover, the cavitation bubbles need to be prevented from forming near or on the ultrasonic transducer surface, thereby blocking the ultrasonic waves.

According to an aspect of some embodiments of the present invention there is provided a catheter for ultrasonic-driven bladder therapeutic agent delivery. In some embodiments, the catheter comprises a tube, one or more transducers mounted on the tube, at least one expandable portion, and a transducer sleeve. In some embodiments, the transducer sleeve is configured to enclose one or more transducers, wherein a volume is defined between the enclosed transducer and walls of the transducer sleeve. In some embodiments, the transducer sleeve is disposed between at least two expandable portions. In some embodiments, the transducer sleeve interconnects at least two expandable portions.

According to some embodiments of the invention, the tube comprises at least one fluid port configured to supply fluid to or remove fluid from at least one of the at least one expandable portion. In some embodiments, the expandable portion is inflated by fluid supplied into the portions via the fluid ports. In some embodiments the transducer sleeve is expandable.

According to some embodiments of the invention, the tube comprises at least one therapeutic fluid port configured to supply therapeutic fluid into the bladder. In some embodiments, the tube comprises at least one therapeutic fluid port at a distal end of the tube. In some embodiments, the tube comprises at least one therapeutic fluid port between the transducer sleeve and either one of the expandable portions. In some embodiments, the tube comprises at least one therapeutic fluid port between the transducer sleeve and a proximal expandable portion. As used herein, the term "Proximal" means close to the operator and away from the subject being treated and the term "Distal" means distant from the operator and towards the subject being treated. In some embodiments, fluid can be removed via the therapeutic fluid port.

In some embodiments the at least one expandable portion at an expanded state is shaped as a sphere or a spheroid. In some embodiments, the at least one expandable portion at an expanded state is toroidal. In some embodiments, the at least one expandable portion at an expanded state comprises a C-shaped cross-section. In some embodiments, the at least one expandable portion at an expanded state comprises an umbrella configuration. In some embodiments, the catheter comprises a expandable portion shaped at an expanded state as a "dog-bone" having two expanded portions interconnected by a transducer sleeve.

In some embodiments, the at least one expandable portion is configured to maintain at least a portion of the internal bladder surface distant from the transducer sleeve. In some embodiments, the transducer sleeve defines a lumen and the catheter transverses via the lumen. In some embodiments, one or more transducers are mounted on a portion of catheter inside the transducer sleeve lumen. In some embodiments, the transducer is surrounded by a fluid that occupies a volume defined between the transducer and the transducer sleeve surrounding the transducer. In some embodiments of the invention, the fluid cools the enclosed transducers. In some embodiments the fluid is an acoustic fluid for an efficient delivery of acoustic waves produced by a transducer.

According to some embodiments, the transducer sleeve at an expanded state is cylindrical. In some embodiments, the maximal cross-sectional area of the transducer sleeve at an expanded state is smaller than the maximal cross-sectional area of any one of the expandable portions at an expanded state at any point along their longitudinal axis. In some embodiments, the maximal cross-sectional area of the transducer sleeve at an expanded state is two thirds of a maximal cross-sectional area of the expandable portions at an expanded state at any point along their longitudinal axis. In some embodiments, the maximal cross-sectional area of the transducer sleeve at an expanded state is one third of the maximal cross-sectional area of the expandable portions at an expanded state at any point along their longitudinal axis. According to some embodiments, the tube, at least one of the expandable portions, and the transducer sleeve are concentric.

According to some embodiments of the invention, the expandable portions are configured to occupy a portion of the bladder volume at an inflated state, while defining a treatment volume defined by the transducer sleeve wall, walls of the expanded portions disposed at each end of the transducer sleeve and the bladder wall. In some embodiments, the expandable portions occupy at least one half of the bladder volume at an inflated state. In some embodiments, the expandable portions occupy between one third and two thirds of the bladder volume when bladder is at an inflated state. This configuration directs a therapeutic agent containing fluid within the bladder into the treatment volume in the vicinity of the transducer, while protecting sensitive regions of the bladder e.g., the vesical trigone, at the internal surface of the bladder from being treated by the therapeutic agent and/or being affected by energy transmitted by the transducer. In some embodiments of the invention, at least some of the expandable portions are configured to apply pressure on internal surfaces of the bladder at an expanded state.

According to some embodiments of the invention, at least one of the expandable portions is configured to engage the bladder wall at an expanded state and block drainage of fluid from the treatment volume to between the expandable portions and the bladder wall. In some embodiment, an expandable portion at an expanded state maintains the tube concentric with the bladder wall.

According to some embodiments of the invention, the expandable portions and the transducer sleeve are portions of the same balloon mounted on the tube. In some embodiments, the transducer sleeve is inelastic having fixed expanded dimensions. In some embodiments, the transducer sleeve is rigid or comprises a stiffening element.

According to some embodiments of the invention, the catheter comprises a gap between the transducer and the tube. In some embodiments, the gap is in the range of 0.05 mm to 4 mm. According to some embodiments, the gap is in the range of 0.1 mm to 2.5 mm. In some embodiments the transducer is connected to the tube via spacers.

According to an aspect of some embodiments of the present invention there is provided a catheter for ultrasonic-driven bladder therapeutic agent delivery. The catheter comprises a tube, a proximal expandable portion, one or more transducers mounted on the tube between the proximal expandable portion and a distal end of the tube and a transducer sleeve enclosing one or more of the transducers. In some embodiments, the transducer sleeve has deflated state and an expanded state.

In some embodiments, the proximal expandable portion and the transducer sleeve comprise distinct balloons. In some embodiments, the proximal expandable portion and the transducer sleeve comprise portions of one balloon. In some embodiments the proximal expandable portion at an expanded state is shaped as a sphere or spheroid. In some embodiments the proximal expandable portion at an expanded state is shaped as a toroid. In some embodiments, at least one of the proximal expandable portions at an expanded state comprises a C-shaped cross-section. In some embodiments, at least the proximal expandable portions at an expanded state comprises an umbrella configuration.

According to some embodiment of the invention, the tube comprises at least one therapeutic fluid port configured to supply therapeutic fluid into the bladder. In some embodiments, the therapeutic fluid port is located between the transducer sleeve and the proximal expandable portion. In some embodiments, fluid can be removed via the therapeutic fluid port.

According to some embodiments, the proximal expandable portion comprises a balloon that at an expanded state holds the tube at a pre-defined position within the bladder. In some embodiments the proximal expandable portion is configured to engage the bladder wall at an expanded state and block a drainage of fluid from a treatment volume within the bladder to between the proximal expandable portion wall and the bladder wall.

According to some embodiments of the invention, the transducer sleeve at an expanded state is cylindrical having a uniform cross section at least at a portion of its length. In some embodiments, the maximal cross-sectional area of the transducer sleeve at an expanded state is smaller than the maximal cross-sectional area of the proximal expandable portion at an expanded state at any point along their longitudinal axis. In some embodiments, the maximal cross-sectional area of the transducer sleeve at an expanded state is two thirds of a maximal cross-sectional area of the proximal expandable portion at an expanded state at any point along their longitudinal axis. In some embodiments, the maximal cross-sectional area of the transducer sleeve at an expanded state is less than 50% the maximal cross-sectional area of the proximal expandable portion at an expanded state at any point along their longitudinal axis. According to some embodiments, the tube, the proximal expandable portion, and the transducer sleeve are concentric.

According to some embodiments of the invention, the transducer sleeve at an expanded state does not intersect with an imaginary cone extending between an apex located at the distal end of the tube, and a plane defined by the circumference of the expandable portion at an expanded state. According to some embodiment of the invention, the transducer sleeve is inelastic having limited expanded dimensions. In some embodiments, the transducer sleeve is rigid or comprises a stiffening element.

In some embodiments, the therapeutic agent fluid may be a non-gassed fluid. However, in some embodiments, the amount of cavitation bubbles generated in the therapeutic agent fluid are increased by providing a gassed therapeutic agent fluid. Therefore, according to an aspect of some embodiments of the present invention there is provided a method for increasing the amount of cavitation bubbles within a therapeutic agent used with a catheter for ultrasonic-driven bladder therapeutic agent delivery. In some embodiments, the method comprises pressurizing a sterile liquid with a gas and generating a "gassed liquid". In some embodiments, the method comprises releasing a therapeutic agent into the gassed liquid and forming a gassed therapeutic fluid. In some embodiments, the method comprises inserting the gassed therapeutic fluid into the bladder via a catheter for ultrasonic-driven bladder therapeutic agent delivery and forming cavitation in the therapeutic fluid. According to some embodiments of the invention, the method comprises, for example pressurizing a sterile liquid with a gas comprises pressurizing at a pressure of about 8 to 30 atmospheres and for a predetermined duration.

In some embodiments, the therapeutic agent fluid is mixed with a non-gassed fluid instead of a gassed fluid.

In some embodiments, the catheter comprises an expandable portion such as a balloon, a stent, or any combination thereof. In some embodiments, at least one expandable portion comprises a stent.

Figure 1B:
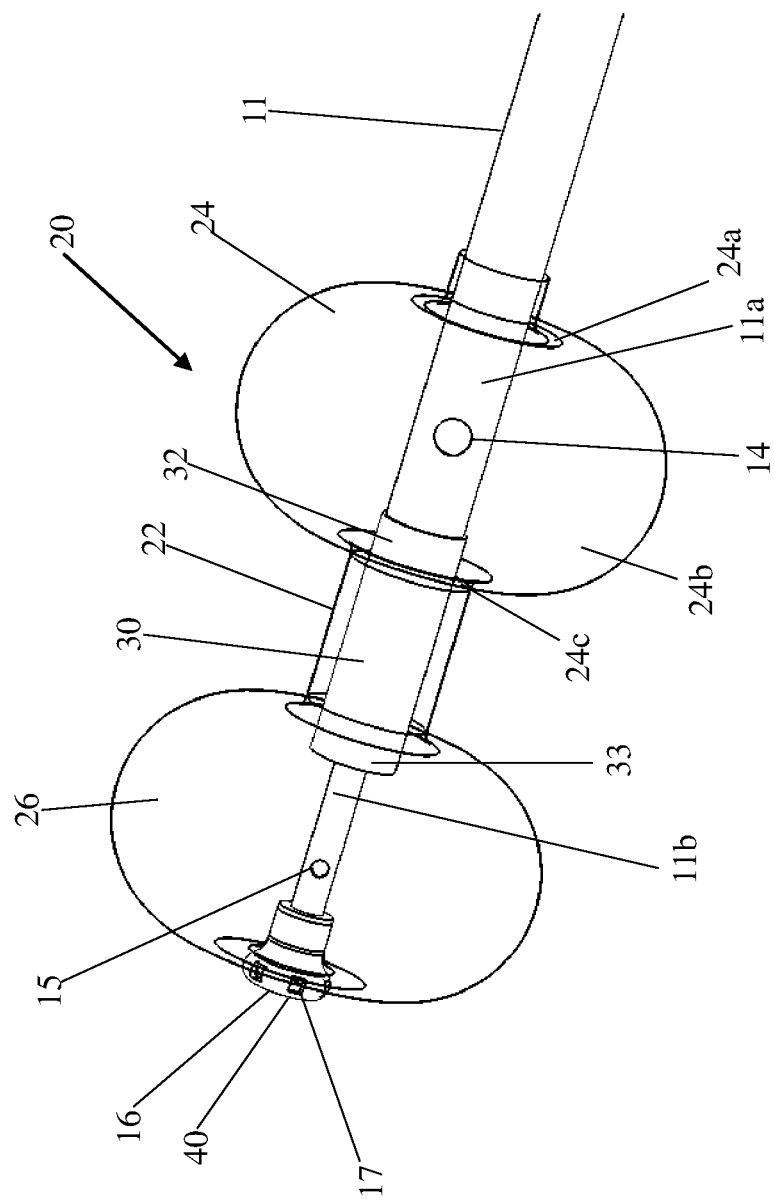

Reference is now made to FIGS. 1A and 1B, collectively referred to as FIG. 1, which is a side view with a perspective enlarged view, simplified illustration of a catheter for ultrasonic-driven bladder therapeutic agent delivery in accordance with some embodiments of the invention. As shown in FIG. 1, a catheter 10 comprises a tube 11, a transducer 30 mounted on tube 11 and an expandable portion 20 mounted on tube 11 and enclosing transducer 30. In the exemplary embodiment depicted in FIG. 1, the expandable portion 20 is a balloon. In some embodiments, expandable portion 20 comprises two expandable portions 24 and 26 coupled to and sandwiching a transducer sleeve 22 disposed in between. The tube 11 comprises at least one fluid ports 14 and 15, configured to supply or to remove fluid out of at least one of the balloon 20 portions 22, 24 and 26. The transducer sleeve 22 encapsulates the transducer 30 and defines a volume between the walls of the transducer sleeve 22 and the transducer.

In some embodiments, the tube comprises one or more conduits, or in other words, fluid supply channels, (not shown) supplying fluid from a fluid source to one or more ports. The terms "conduits" and "fluid supply channels" as used herein are interchangeable. The one or more fluid supply channels are disposed inside the tube or along an outer surface of the tube. In some embodiments, a fluid flow is generated within the balloon 20 and at least within the internal volume of the transducer sleeve 22 by providing fluid via one of the fluid ports, e.g. port 14, and removing fluid via another fluid port, e.g. port 15.

In some embodiments, the fluid provided into the balloon comprises an acoustic fluid. The term "acoustic fluid", as referred to herein, relates to a fluid with high cavitation energy threshold to prevent formation of cavitation bubbles in this liquid during operation of the ultrasound that would interfere with acoustic waves, and prevent damage to the catheter. The acoustic fluid allows efficient progression of ultrasound energy. An aspect of this fluid is that it reduces cavitation, which may block ultrasound energy from progressing from the transducer to the bladder internal surface. Such fluid may be a degassed fluid, e.g. a degassed solution such as saline which went through boiling, or a solution which its gas content was filtered out. The acoustic fluid assists in transmitting the acoustic waves produced by the transducer 30 through the surface of the transducer sleeve 22 to the therapeutic fluid surrounding the transducer sleeve. The acoustic fluid can also cool the enclosed transducers 30, for example by heat convection. By the cooling of the transducers, the transducers can be operated in desired parameters for a longer treatment duration. In addition, the overheating of the bladder tissues by heated transducers is avoided.

The acoustic fluid provided into the transducer sleeve 22 does not contain gas bubbles to serve as nucleation seeds for the generation of cavitation and therefore distances the cavitation phenomenon from the transducer 30 and towards the bladder wall. The ultrasound waves travel from the transducer through the acoustic fluid without generating cavitation, hence are free to travel through this medium towards the surface of the sleeve 22. Then, the waves travel through the therapeutic fluid located in a therapeutic volume between the sleeve and the bladder towards the bladder tissue. In the therapeutic fluid cavitation is generated, thereby, resulting in the delivery of the therapeutic agent into the bladder. This allows the transducer to be disposed farther from the bladder internal surface than transducers exposed to therapeutic fluid inside the bladder. Production of cavitation increases the efficacy of the ultrasound treatment as described in detail in U.S. patent application Ser. No. 15/561,733 to the same inventors.

As shown in the exemplary embodiment depicted in FIG. 1 and View A of FIG. 1, the tube 11 comprises a tip 16 which comprises a plurality of fluid port(s) 17. In some embodiments, tip 16 is convex and configured to allow easier insertion of the catheter into the bladder and reduce accidental damage to the interior surface of the bladder during the deployment of the catheter within the bladder. In some embodiments, tip 16 has oblong geometry having fluid ports at a distal end of the tip. In some embodiments, tip 16 has no ports. The bladder fluid ports 17 can be used, for example, for one or more of the following functions: inserting therapeutic fluid into the bladder, removing therapeutic fluid out of the bladder, inserting tissue cleaning fluid, such as saline to remove a therapeutic fluid, and removing fluid out of the bladder, e.g. urine filling a urine bladder prior to treatment. In some embodiments, the shape of tip 16 is one of a toroid, torus, disk, sphere, and semi-sphere. In some embodiments, the tip 16 is rigid or semi-rigid. In some embodiments, the port(s) 17 are distributed along at least a portion of the circumference of the tip 16. In some embodiments, the tip 16 comprises a surface 40 positioned distally in relation to the port(s) 17. In some embodiments, the surface 40 is rounded. In some embodiments, the tip 16 is blind. In some embodiments, fluid flowing within tube 11 exits port(s) 17.

A potential advantage of a plurality of openings (ports) is in that multiple ports provide a redundancy in cases of clogged ports when inserting or removing fluid. In some embodiments in which the transducer sleeve and an expandable portion are disposed on distinct balloons, at least one therapeutic fluid port can be disposed at the tube, between the transducer sleeve and the expandable portion. In some embodiments, at least one therapeutic fluid port can be disposed at the tube at a proximal tube portion which is not covered by any expandable portion.

In some embodiments, the fluid port(s) 17 are positioned radially around the longitudinal axis of the catheter and/or tube. In some embodiments, the fluid port(s) 17 are positioned such that a fluid streaming from the fluid port(s) 17 is ejected at a nonzero angle in relation to the longitudinal axis of the catheter and/or tube.

For example, in the exemplary embodiment depicted in FIG. 1 and View A of FIG. 1, when the catheter 10 is inserted into a bladder such that tip 16 is urged against the wall of the bladder (e.g., the surface opposite the trigone) marked region 5", or other portions of the urinary bladder wall, the bladder wall does not obstruct the fluid port(s) 17.

In some embodiments, the tip 16 comprises a distal opening of the distal portion 11*b* of tube 11. In some embodiments, the tip 16 comprises at least one port 17 at the surface 40. In some embodiments, the tip 16 comprises a cover comprising at least one aperture, such as a mesh. In some embodiments, the tip 16 cover is rigid or semi rigid. In some embodiments, the cover defines a volume around the tip 16.

For example, in some embodiments, when the catheter 10 is inserted into a bladder such that the cover of tip 16 is urged against the wall of the bladder, for example, the distal portion of the bladder (such as the surface opposite the trigone) marked region 5", or other portions of the urinary bladder wall, the bladder wall does not obstruct at least one aperture of the tip 16 cover.

In some embodiments, at least one of the transducer, at least one of the expandable portion, and the tube are concentric. In some embodiments, at least two expandable portions are concentric. In some embodiments, the transducer and at least one expandable portion are concentric. In some embodiments, the transducer sleeve and at least one expandable portion are concentric. In some embodiments, the transducer sleeve and the transducer are concentric.

An advantage of the concentric positions of the catheter, expandable portion, transducer sleeve and/or transducer is in that the catheter maintains equal distance between the internal bladder wall and the transducer, such that the treated portion of the bladder wall may receive equal or nearly-equal treatments. Additionally, in some embodiments, the treated portion of the bladder wall may receive predetermined varying treatment.

In some embodiments, the tube 11 comprises one or more conduits which supply fluid to one or more of the ports 14/15/17. In some embodiments, each conduit opens to a specific port 14/15/17. In some embodiments, each conduit opens to a separate port 14/15/17. In some embodiments, a conduit opens to at least one of the ports 14/15/17.

In some embodiments, tube lumen 11 comprises at least one conduit. In some embodiments, at least one conduit is in fluid communication with a proximal opening 34/36/38 of the catheter 10.

In some embodiments, the catheter 10 comprises at least one proximal opening 34/36/38 through which fluid passes into and/or out of one or more ports 14/15/17. In some embodiments, a proximal opening 34/36/38 is in fluid communication with a reservoir for fluid, such as, for example, a therapeutic fluid, a fluid (e.g. saline), a gassed fluid, and an acoustic fluid. In some embodiments, a proximal opening 34/36/38 is in fluid communication with a drainage bag. In some embodiments, at least one conduit is coupled to one or more of the proximal openings 34/36/38. In some embodiments, each of the proximal openings 34/36/38 is in fluid communication with at least one of the ports 14/15/17.

Figure 2:
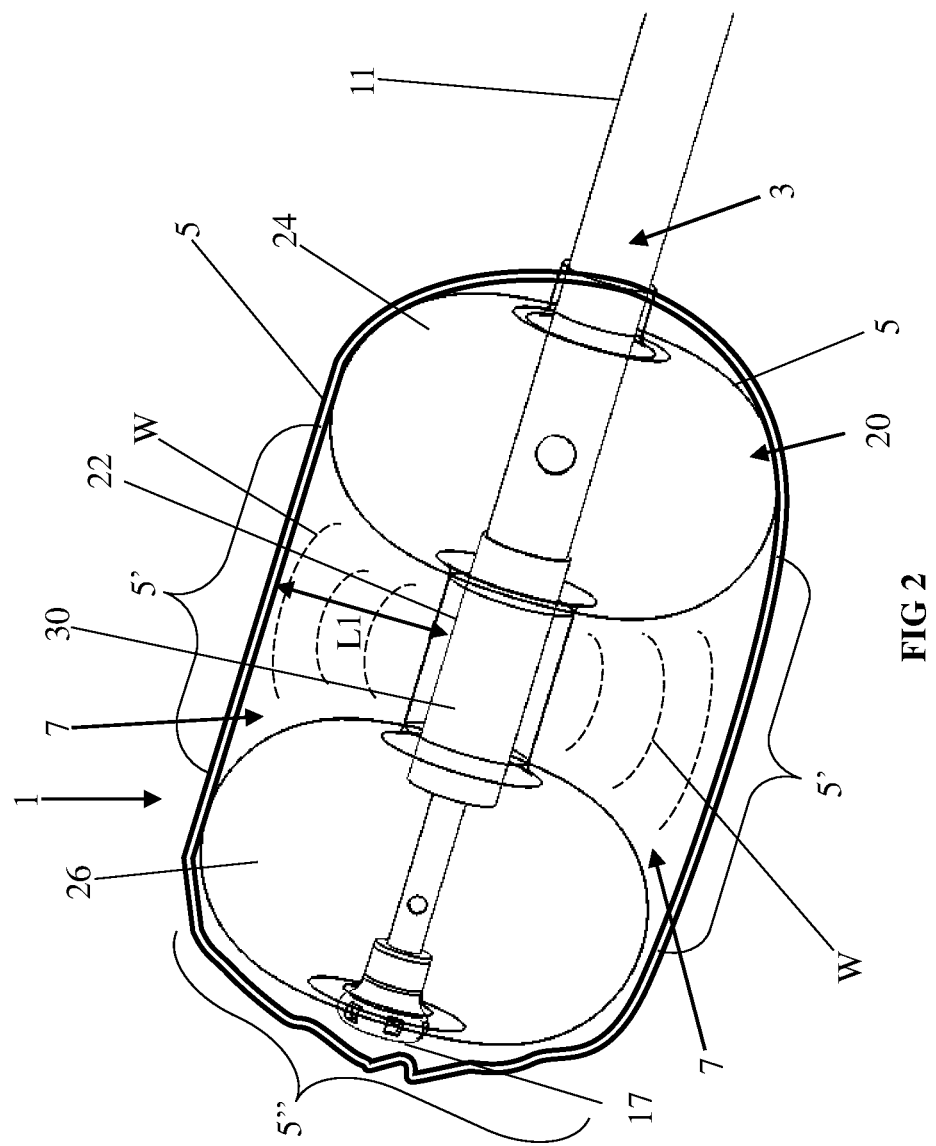
FIG. 2 is a perspective view simplified illustration of a catheter for ultrasonic-driven bladder therapeutic agent delivery in accordance with some embodiments of the invention.

FIG. 2 is a perspective view simplified illustration of implementation of an ultrasonic-driven bladder therapeutic agent delivery inside a bladder 1 in accordance with some embodiments of the invention. In the exemplary embodiment depicted in FIG. 2, expandable portions 24 and 26 are spheroid in geometry and in an expanded state. In some embodiments, both expandable spheroid portions 24 and 26 occupy a portion of the bladder volume, thereby forming a treatment volume 7 surrounding the transducer sleeve 22 between the expandable spheroid portions 24 and 26 and the bladder wall 5. A potential advantage of this configuration is in that a therapeutic agent disposed within the bladder 1 will be directed into the treatment volume 7 between the transducer 30 and the bladder wall 5, limiting the treatment on bladder tissues to section 5' of the bladder wall and the treatment volume 7 and benefiting from the full effect of cavitation formed by transducer 30. Additionally, in some embodiments, this configuration directs a therapeutic agent containing fluid within the bladder 1 into the treatment volume 7, while protecting regions e.g., the vesical trigone, at the internal surface of the bladder 1 from being treated by the therapeutic agent and/or energy transmitted by the transducer 30. In some embodiments, the expandable portions 24 and 26 occupy between 30% and 70% of the bladder volume at an expanded state. In some embodiments, the expandable portions 24 and 26 occupy between 40% and 60% of the bladder volume at an expanded state.

Normally, in a relaxed state, a bladder wall is undulated in shape. In some embodiments, the inflated balloon 20 applies tension in the internal surface 5 of the bladder 1 in a plurality of directions, thereby straightening at least a portion of the bladder wall of the bladder at least in region 5' bordering the treatment volume 7 between expandable portion 24 and 26 as shown in FIG. 2.

Since the expanded balloon has a predictable geometry and dimensions at a pre-defined pressure, the measurements of the treatment volume 7 surrounding the transducer 30 are also predictable. Expandable portions 24 and 26 can be designed to have a circumference at a fully expanded state that will define a pre-determined distance L1 between the transducer 30 and the bladder treated surface 5'. In some embodiments, a uniform treatment is achieved by having the treated tissues at equidistance from the transducer. In some embodiments, the concentration of the therapeutic agent within the therapeutic fluid are determined by the predictable treatment volume 7. Straightening and stretching the bladders' tissues contribute to the efficacy of the treatment by increasing the permeability of the therapeutic agent into the bladder tissues. In addition, such structural configuration stabilizes the bladder wall and increases the safety of the procedure by preventing the collapse of the bladder wall onto or close to the hot transducer surface. In addition, the transducer sleeve 22 prevent a direct contact between the bladder and the transducer 30.

In some embodiments, and as described in greater detail elsewhere herein, one or more of the expandable portions is a stent.

In some embodiments, e.g., in treatment of the urinary bladder, the procedure is carried out when the bladder is positioned vertically or close to vertically wherein the trigone is lowest portion of the urinary bladder. In some embodiments, as shown in FIG. 2, the distal expandable portion 26 does not seal a distal portion of the bladder (e.g., the surface opposite the trigone) marked region 5". The therapeutic fluid provided through ports 17 can then flow into the volume 7, e.g. by gravity or by pressure gradient. In some embodiments, the proximal expandable portion 24, as illustrated in FIG. 2, engages the proximal surface of the bladder. At an expanded state, the expandable portion 24 can block a drainage of fluid from the therapeutic volume 7 being pressed against the bladder wall. The expandable portion 24 can be pressed against and seal the proximal surface of the bladder (e.g. by static forces, such as gravity, fluid pressure, distal spheroid pressing against a distal bladder surface). Thereby, the therapeutic fluid remains within the therapeutic volume 7 during the treatment, while bladder tissues located beyond the expandable portion 24 are protected from being exposed and treated by the therapeutic fluid and the acoustic energy.

In some embodiments, the proximal and/or distal expandable portion 24/26 shields portions of the bladder wall from ultrasonic energy. In some embodiments, the proximal expandable portion 24 shields the trigone from ultrasonic energy. In some embodiments, the proximal and/or distal expandable portion 24/26 acts as a vessel for a cooling fluid flow which increases heat dissipation from the transducer.

In some embodiments, at least one of the proximal and/or distal expandable portion 24/26 is filled with fluid which has high acoustic impedance and therefore is non-conducive to ultrasound energy. In some embodiments, the non-conducive fluid inflates at least one of the proximal and/or distal expandable portion 24/26. In some embodiments, the non-conducive fluid prevents transmission of ultrasound energy to the untreated areas of the bladder (e.g., the trigone).

A potential advantage of having the non-conducive fluid within one or more expandable portions 24/26 is in that ultrasound energy is not transmitted to portions of the bladder which are not treated.

In some embodiment of the invention, expandable portion 24 serves as a catheter support and fixes the position of the tube 11 within the bladder 1. In some embodiments, fluid within one or more expanded portions engaging an internal surface 5 of the bladder 1, cools the bladder by heat transfer between the bladder wall and the fluid.

In some embodiments, the volume and/or shape of the expandable portions 24/26 determine the distance between the bladder treated surface 5' and the transducer 30. In some embodiments, the volume and/or shape of the expandable portions 24/26 determine the distance between the bladder treated surface 5' and the transducer sleeve 22. In some embodiments, the distance between the bladder treated surface 5' and the transducer 30 and/or the transducer sleeve 22 is predetermined.

The temperature of the bladder treated surface 5' is correlated with the heat given off by the transducer. Therefore, increasing the distance between the transducer 30 and the bladder treated surface 5' prevents over-heating of the bladder treated surface 5'. In some embodiments, increasing the distance between the transducer 30 and the bladder treated surface 5' permits heating of the transducer 30 to higher temperatures, for example, by increasing on-time and/or frequency emitted by the transducer.

In some embodiments, increasing the frequency emitted by the transducer increases the efficacy of the treatment by increasing the cavitation within the therapeutic fluid (and/or combination of the gassed fluid and therapeutic fluid). In some embodiments, increasing the on-time of the transducer increases the efficacy of the treatment by increasing the cavitation within the therapeutic fluid (and/or combination of the gassed fluid and therapeutic fluid).

Figure 3:
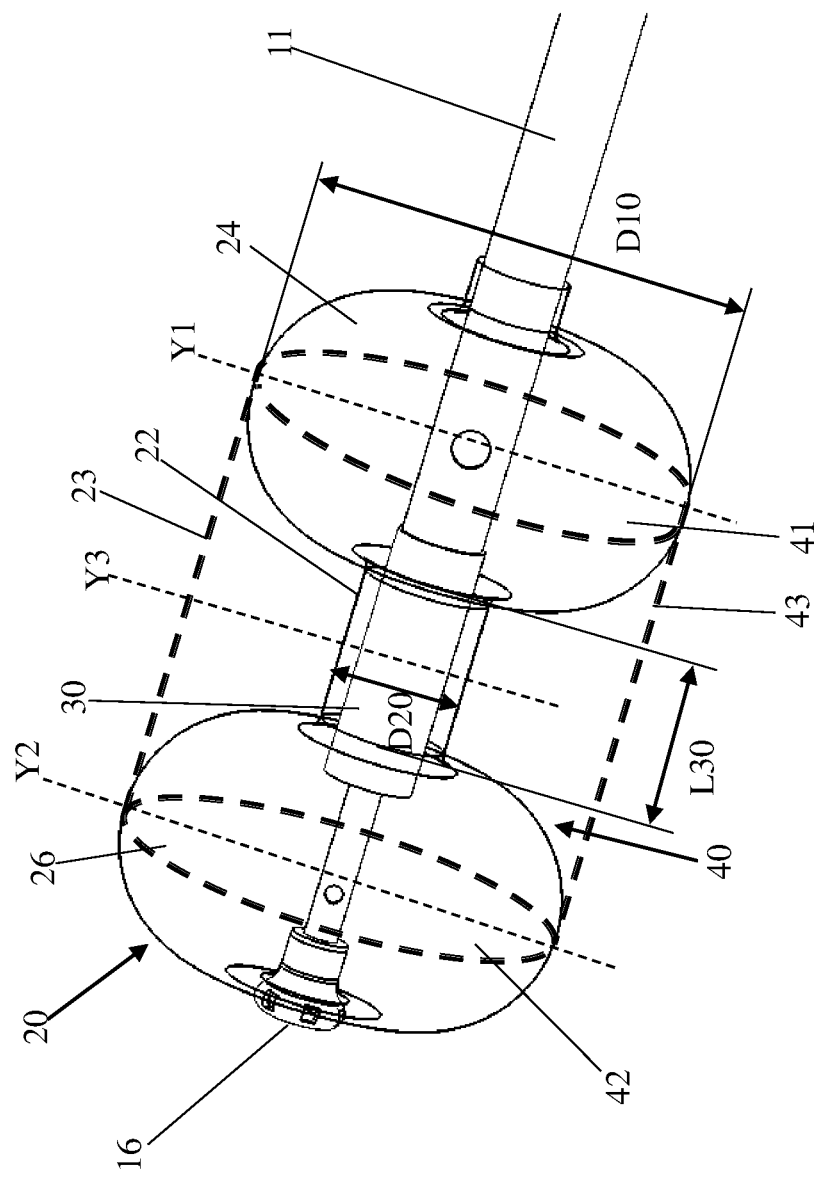
FIG. 3 is a perspective view simplified illustration of a catheter for ultrasonic-driven bladder therapeutic agent delivery in accordance with some embodiments of the invention.

As shown in FIG. 3, according to some embodiment of the invention, expandable portions 24 and 26 define a cylinder 23 therebetween, the wall of the cylinder outlined by broken lines, congruent with the largest circumference of the expandable portions 24/26 at Y1 and Y2 respectively. In some embodiments and as explained in detail elsewhere herein, the maximal cross-sectional area of the transducer sleeve 22 taken at Y3 is smaller than the maximal cross-sectional area of the expanded portions 24 and 26. In some embodiments a diameter D10 of expandable portions 24 and 26 is between 20 mm and 40 mm at an expanded state. In some embodiments, a diameter D10 of expandable portions 24 and 26 is between 20 and 40 mm at an expanded state. In some embodiments, a diameter D20 of a transducer sleeve 22 is between 5 mm and 15 mm. In some embodiments, a diameter D20 of a transducer sleeve 22 is between 6 mm and 12 mm. In some embodiments, a diameter D20 of a transducer sleeve 22 is between 8 mm and 10 mm. In some embodiments a length L30 of the transducer sleeve is between 5 and 25 mm at an expanded state. In some embodiments a length L30 of the transducer sleeve is between 10 and 15 mm at an expanded state.

In some embodiments, the transducer sleeve at an expanded state is cylindrical having a uniform cross section at least at a portion of its length. In some embodiments, the maximal cross-sectional area of the transducer sleeve at an expanded state is smaller than the maximal cross-sectional area of the proximal expandable portion at an expanded state at any point along their longitudinal axis. In some embodiments, the maximal cross-sectional area of the transducer sleeve at an expanded state is two thirds of a maximal cross-sectional area of the proximal expandable portion at an expanded state at any point along their longitudinal axis. In some embodiments, the maximal cross-sectional area of the transducer sleeve at an expanded state is less than 50% the maximal cross-sectional area of the proximal expandable portion at an expanded state at any point along their longitudinal axis. According to some embodiments, the tube, the proximal expandable portion, and the transducer sleeve are concentric.

In some embodiments, the length of the transducer 30 is 3-20 mm. In some embodiments, the length of the transducer 30 is 4-14 mm. In some embodiments, the length of the transducer 30 is 5-10 mm. In some embodiments, the length of the transducer 30 is 6 mm.

In some embodiments, the width of the transducer 30 is 3-14 mm. In some embodiments, the width of the transducer 30 is 3-7 mm. In some embodiments, the width of the transducer 30 is 3-5 mm. In some embodiments, the width of the transducer is 4 mm.

In some embodiments, the thickness of the transducer 30 is 10-40 mm. In some embodiments, the thickness of the transducer 30 is 15-30 mm. In some embodiments, the thickness of the transducer 30 is 15-23 mm. In some embodiments, the thickness of the transducer 30 is 20 mm.

In some embodiments, the balloon wall comprises regions having variable elasticity so that, for example, only portions of the balloon wall are elastically expandable. E.g. diametrically opposed faces 24a and 24c (FIG. 1) of expandable portion 24 can be produced as an inelastic face, while a face 24b along the circumference of expandable portion 24 is elastically flexible, hence the expansion of portion 24 will be greater radially expansion along catheter tube 11.

In some embodiments at least one of the expandable portions at an expanded state is shaped as at least one of a sphere, a spheroid and a toroid. In some embodiments, at least one of the expandable portions at an expanded state comprises a C-shaped cross-section. In some embodiments, at least one of the expandable portions at an expanded state comprises an umbrella configuration.

In some embodiments, the transducer sleeve at an expanded state is cylindrical. In some embodiments, the maximal cross-sectional area of the transducer sleeve at an expanded state is smaller than the maximal cross-sectional area of any one of the expandable portions at an expanded state at any point along their longitudinal axis. In some embodiments, the maximal cross-sectional area of the transducer sleeve at an expanded state is two thirds of a maximal cross-sectional area of the expandable portions at an expanded state at any point along their longitudinal axis. In some embodiments, the maximal cross-sectional area of the transducer sleeve at an expanded state is one third of the maximal cross-sectional area of the expandable portions at an expanded state at any point along their longitudinal axis. In some embodiments, the tube, at least one of the expandable portions, and the transducer sleeve are concentric.

In some embodiments of the invention, the expandable portions are configured to occupy a portion of the bladder volume at an inflated state, while defining a treatment volume defined by the transducer sleeve wall, walls of the expanded portions disposed at each end of the transducer sleeve and the bladder wall. In some embodiments, the expandable portions occupy at least one half of the bladder volume at an inflated state. In some embodiments, the expandable portions occupy between one third and two thirds of the bladder volume when bladder is at an inflated state. This configuration directs a therapeutic agent containing fluid within the bladder into the treatment volume in the vicinity of the transducer, while protecting sensitive regions of the bladder e.g., the vesical trigone, at the internal surface of the bladder from being treated by the therapeutic agent and/or being affected by energy transmitted by the transducer. In some embodiments of the invention, at least some of the expandable portions are configured to apply pressure on internal surfaces of the bladder at an expanded state.

In some embodiments, shaping of any of the balloons can done by: molding, differential thickness, varying materials, integral elements, etc. Another method for shaping any of the balloon portions can be by limiting its expansion by external elements, such as a sleeve or a net.

In some embodiments, the tube 11 has a uniform cross section throughout its length. In some embodiments, a distal portion 11b of tube 11 comprises a smaller diameter than the diameter of proximal portion 11a of tube 11. In some embodiments, as shown in view A in FIG. 1, portion 11b comprises the distal tip 16. In some embodiments, portion 11b is connected to tube 11 under a proximal edge of transducer 30. In some embodiments, transducer 30 is mounted on portion 11b of tube 11 so that an external surface of transducer 30 is positioned flush with proximal portion 11a of tube 11. In some embodiments portion 11b comprises a narrow tube portion inserted within tube 11.

In some embodiments, each of ports 14/15 are supplied by distinct fluid supply channel so that supplying fluid to expandable portion 26 via port 15 does not necessarily expand expandable portion 24 and vice versa, even though expandable portions 24/26 are in fluid communication via transducer sleeve 22. In some embodiments port 15 is associated with a distinct fluid supply channel of the tube 11. In some embodiments, port 14 is configured to be closed when providing fluid by port 15. A potential advantage in the configuration of ports 14/15 is in that during deployment, expandable portion 26 is configured to be inflated while expandable portion 24 is still within urethra 3, i.e., without expanding expandable portion within urethra 3, which may be painful to the subject being treated.

Figure 4A:
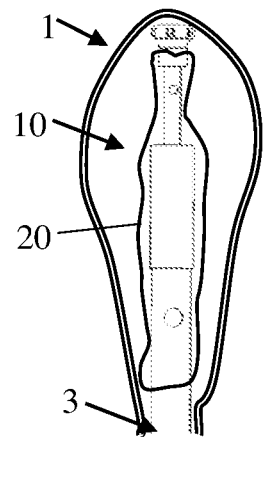
FIGS. 4A-4D are plan view simplified illustrations of a method of implementation of a catheter for ultrasonic-driven treatment of a bladder, in accordance with some embodiments of the invention.
Figure 4B:
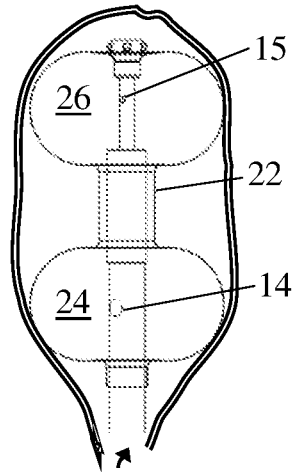
Figure 4C:
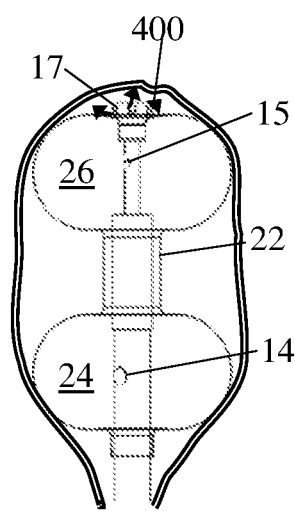
Figure 4D:
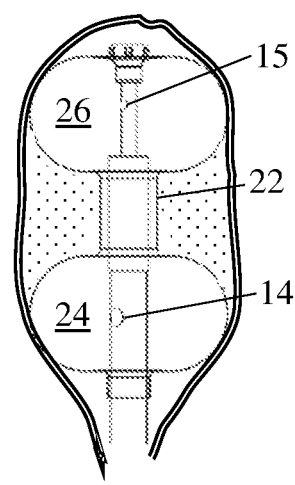

Reference is now made to FIGS. 4A to 4D, which are plan view simplified illustrations of the method of implementation of a catheter for ultrasonic-driven treatment of a bladder. As shown in FIGS. 4a to 4d, the catheter for ultrasonic-driven treatment of a bladder is deployed by:

Inserting (as shown in FIG. 4A) a catheter 10 into bladder 1 through a urethra 3;

Expanding (FIG. 4B) balloon 20, including expandable portions 24, 26 and transducer sleeve 22, to a pre-determine pressure or volume by a pressurized acoustic fluid (e.g. 20 cc-40 cc of fluid) and keeping expanded portions 24/26 and transducer sleeve 22 at an expanded state;

Draining the bladder 1 of fluid through therapeutic fluid port(s) 17;

Supplying saline through therapeutic fluid port(s) 17;

Mixing therapeutic fluid with gassed liquid as described elsewhere herein (this step can be performed any time prior or during the deployment of the catheter); and Supplying (FIG. 4C) a therapeutic fluid (e.g. 20-40 cc) into the bladder via therapeutic fluid port(s) 17. In some embodiments, such as depicted by arrow 400, therapeutic fluid is supplied via therapeutic fluid port(s) 17 into the bladder lumen.

Figure 5:
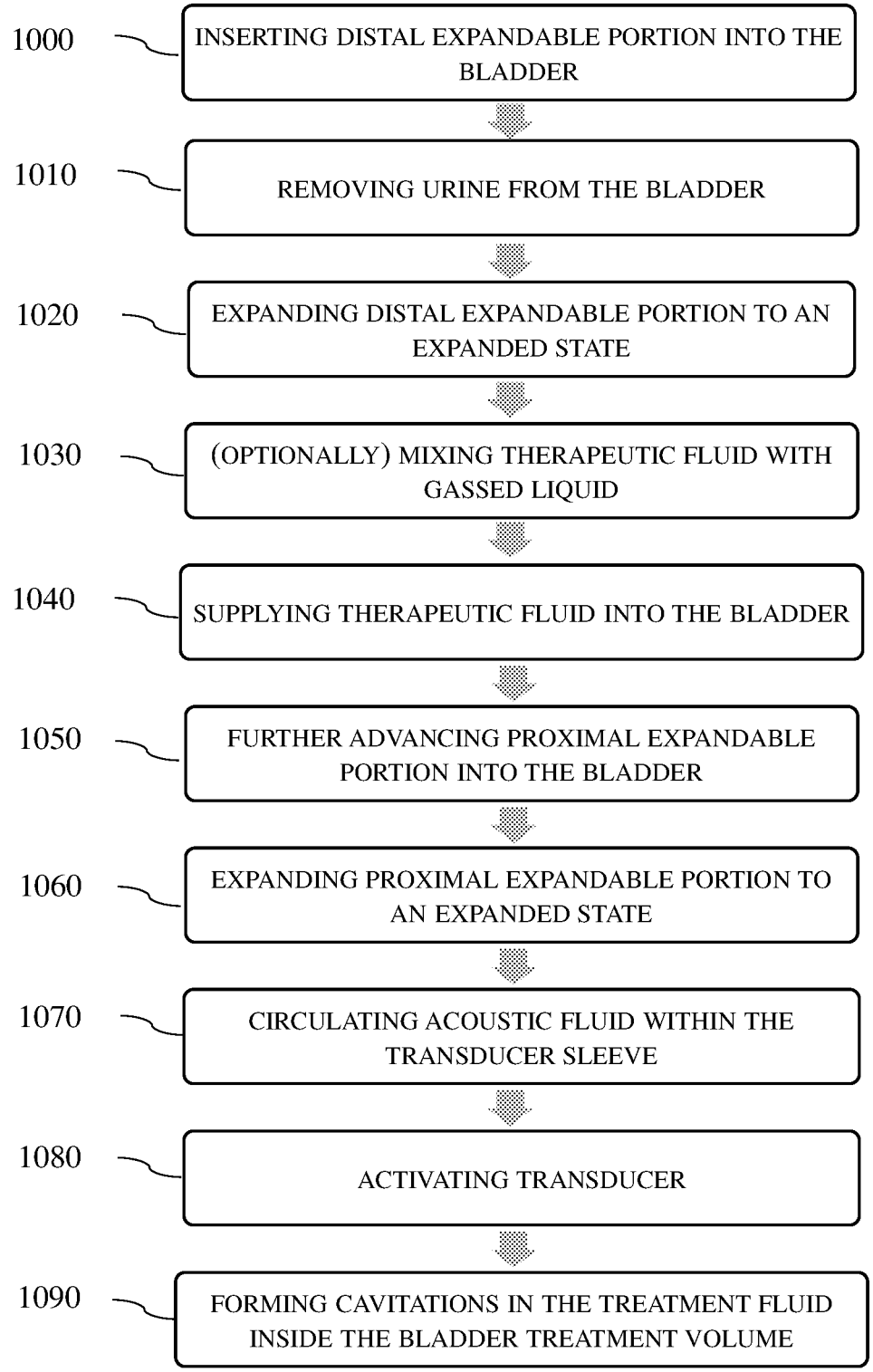
FIG. 5 a flow chart of a method for deploying of a catheter for ultrasonic-driven treatment of a bladder wall, in accordance to some embodiments of the invention.

Reference is now made to FIG. 5, which is a flow chart of a method for deploying of a catheter for ultrasonic-driven treatment of a bladder wall in accordance to some embodiments of the invention and to corresponding FIGS. 6A to 6E, which are side-view simplified illustrations of the method of implementation of a catheter for ultrasonic-driven treatment of a bladder. As shown in FIG. 5, the catheter 10 for ultrasonic-driven treatment of a bladder 1 is deployed by:

Inserting at step 1000 distal expandable portion 26 of catheter 10 into bladder 1 through urethra 3;

Removing at step 1010 urine from the bladder via port(s) 17;

Expanding at step 1020 portion 26 to an expanded state by providing fluid into portion 26 via port 15;

Optionally, Mixing at step 1030 therapeutic fluid with gassed liquid as described elsewhere herein (this step can be performed any time prior or during the deployment of the catheter);

Supplying at step 1040 therapeutic fluid through the therapeutic fluid port(s) 17;

Further advancing at step 1050 proximal expandable portion 24 into bladder 1 through urethra 3; and Expanding at step 1060 proximal expandable portion 24 to an expanded state by providing fluid via port 14.

In some embodiments, the method comprises expanding the proximal expandable portion and trapping the therapeutic fluid between the distal expandable portion and the proximal expandable portion.

A potential advantage in using the method for deployment of the ultrasonic-driven catheter 10 is in that most of the therapeutic fluid does not remain trapped at a distal volume between the distal expandable portion 26 and the bladder wall 5" opposite to the bladder trigone.

FIG. 6A is a plan view simplified illustration of the insertion of distal expandable portion 26 into bladder 1 through urethra 3. In some embodiments, the proximal expandable portion 24 remains within the urethra 3.

FIG. 6B is a plan view simplified illustration of the expanding of distal expandable portion 26 to an expanded state by providing fluid into distal expandable portion 26 via fluid port 15 (for example, as depicted by arrow 600). In some embodiments, the distal expandable portion 26 and the proximal expandable portion 24 are in fluid communication. The fluid remains in distal expandable portion 26, flow in the direction of proximal expandable portion 24 countered by external pressure applied to proximal expandable portion 24 by the urethra wall. Accordingly, the proximal expandable portion 24 remains contracted within the urethra due to pressure applied to the proximal expandable portion 24 by the urethra walls. In some embodiments, the proximal expandable portion 24 remains mostly contracted within the urethra.

FIG. 6C is a plan view simplified illustration of supplying of therapeutic fluid through the therapeutic fluid port(s) 17. In some embodiments, the method comprises supplying therapeutic fluid through the therapeutic port(s) 17 into the volume 46 defined by the distal expanding portion 26 and the bladder wall (for example, as depicted by arrow 602).

FIG. 6D is a plan view simplified illustration of the further advancing proximal portion 24 into bladder 1 through urethra 3. In some embodiments, during the further advancement of the proximal portion 24 into bladder 1, proximal portion 24 is freed from external pressure applied thereto by the urethra walls and at least a portion of the fluid inside the distal expandable portion 26 flows into the proximal expandable portion 24 to equalize pressures within expandable portions 24 and 26 in accordance with the law of LaPlace. In some embodiments, fluid inside the distal expandable portion 26 flows into the portion of the proximal expandable portion 24 which is within the bladder 1. In some embodiments, the volume of the distal expandable portion 26 decreases due to fluid flow into the proximal expandable portion 24. In some embodiments, the decrease in volume of the distal expandable portion 26 increases flow of therapeutic fluid into the bladder volume 48 surrounding the transducer sleeve 22. In some embodiments, the decrease in volume of the distal expandable portion 26 creates or increases a distance 50 between the distal expandable portion 26 and the bladder wall, which increases flow of therapeutic fluid to volume 48. In some embodiments, the partially expanded proximal expandable portion 24 provides a barrier for therapeutic fluid flowing into volume 48.

FIG. 6E is a plan view simplified illustration of the expanding of portion 24 to an expanded state by providing fluid into portion 24 via fluid port 14 (for example, as depicted by arrow 604). In some embodiments, expanding proximal expandable portion 24 to an expanded state by providing fluid via port 14 increases the volumes of both the proximal and distal expandable portions 24/26.

In some embodiments, the expandable portions 24/26 are separate balloons. In some embodiments, during or after the further advancement of the proximal portion 24 into bladder 1, at least a portion of the fluid inside the distal expandable portion 26 is removed via fluid port 15. In some embodiments, the volume of the distal expandable portion 26 decreases. In some embodiments, during or after the further advancement of the proximal portion 24 into bladder 1, the proximal expandable portion 26 is at least partially expanded by providing fluid via fluid port 14. In some embodiments, once therapeutic fluid enters the volume 48 surrounding the transducer sleeve 22, the distal expandable portion 26 is expanded by providing fluid into the distal expandable portion 26 via fluid port 15.

In some embodiments, the ultrasonic-driven treatment performed by catheter 10 inserted within a bladder 1 is carried out by a method in accordance with some embodiments of the invention and includes:

Fixing catheter 10 within the bladder 1 by ensuring the expanded balloon portion 24 engages the proximal surface 5 of the bladder 1;

Circulating at step 1070 the acoustic fluid within the transducer portion 22 by providing acoustic fluid via a first fluid port 15 and extracting acoustic fluid via a second fluid port 14;

Activating at step 1080 the transducer 30; and

Forming at step 1090 cavitation in the therapeutic fluid inside the bladder treatment volume.

In some embodiments, the ultrasonic-driven treatment performed by catheter 10 inserted within a bladder 1 is terminated by the following method, according to some embodiments of the invention:

Inactivating transducer 30;

Extracting therapeutic fluid through therapeutic fluid port(s) 17;

Supplying saline through therapeutic fluid port(s) 17 (e.g. to clean the bladder); and Collapsing the expanded portions 26, 22, 24 by releasing or pumping the acoustic fluid out via one or more acoustic fluid ports 14 and 15; and Withdrawing catheter 10 out of the bladder 1 via urethra 3.

Figure 7:
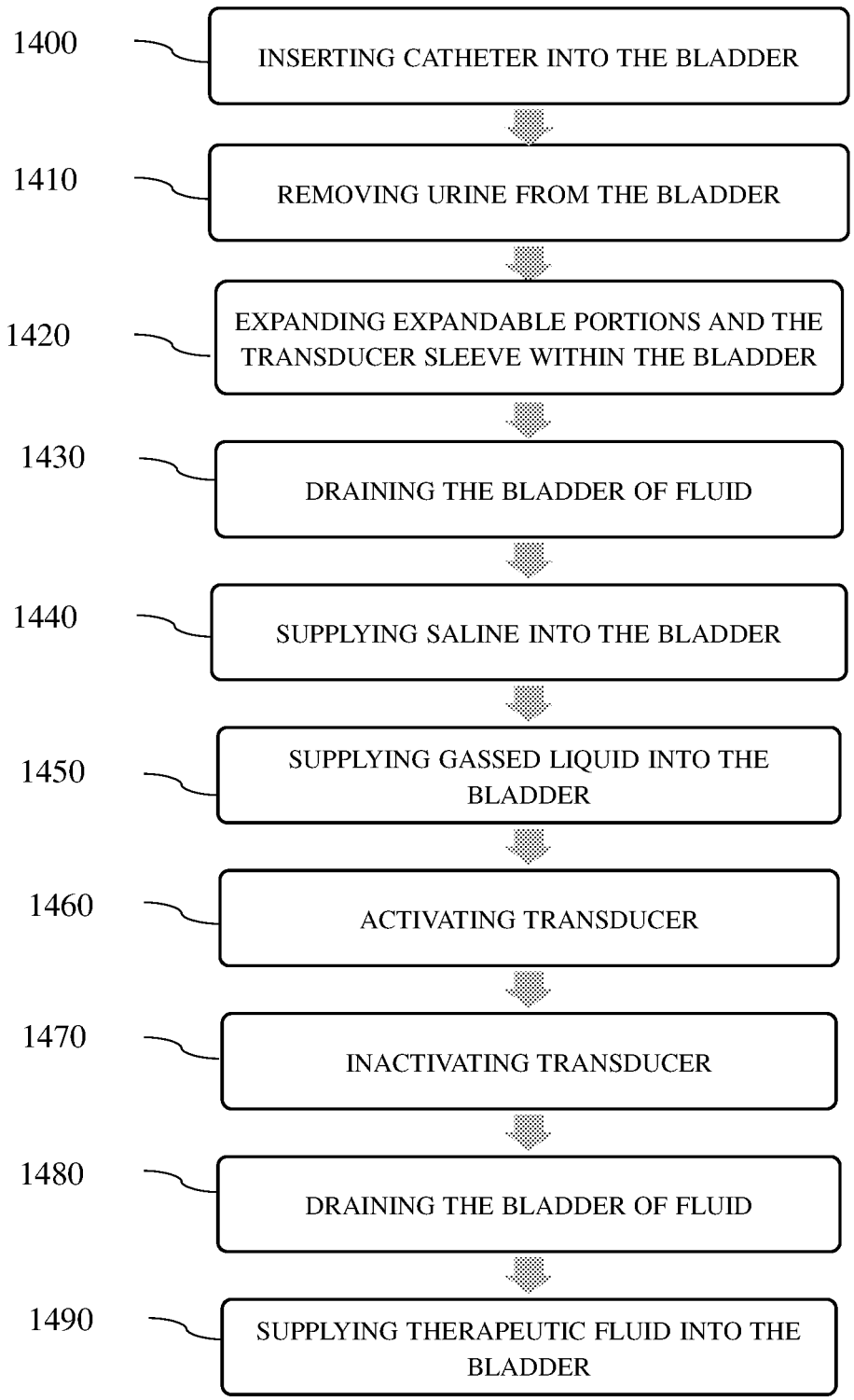
FIG. 7 is a flow chart of a method for deploying of a catheter for ultrasonic-driven treatment of a bladder wall, in accordance to some embodiments of the invention.

Reference is now made to FIG. 7, which is a flow chart of a method for the deployment of a catheter for ultrasonic-driven treatment of a bladder wall and the treatment of the bladder in accordance to some embodiments of the invention. As shown in FIG. 7, the method for deployment of catheter 10 in bladder 1 is carried out as follows:

Inserting at step 1400 catheter 10 into bladder 1 through a urethra 3;

Removing at step 1410 urine from the bladder 1 via port(s) 17;

Expanding at step 1420 expandable portions 24, 26 and transducer sleeve 22, to a pre-determined pressure or volume by a pressurized acoustic fluid (e.g. 20-40 cc of fluid) and keeping expanded portions 24/26 and transducer sleeve 22 at an expanded state; and Optionally, draining at step 1430 the bladder of fluid through therapeutic fluid port(s) 17.

In some embodiments of the invention and as further shown in FIG. 7, deployment of the catheter is followed by a method of treatment of the bladder comprising:

Supplying at step 1440 saline through therapeutic fluid port(s) 17;

Supplying at step 1450 an optionally gassed liquid as described elsewhere herein through bladder therapeutic fluid port(s) 17;

Activating at step 1460 the transducer 30;

Inactivating at step 1470 transducer 30;

Draining at step 1480 the bladder of the optionally gassed fluid through therapeutic fluid port(s) 17;

Supplying at step 1490 a therapeutic fluid (e.g. 20-40 cc) through therapeutic fluid port(s) 17.

In some embodiments, the method comprises expanding the proximal expandable portion and trapping the therapeutic fluid between the distal expandable portion and the proximal expandable portion.

In summary and in accordance with some embodiments of the invention treatment of the bladder comprises at least the following methods:

Method A in which:

deploying a catheter for ultrasonic-driven treatment of a bladder wall in a bladder;

supplying therapeutic fluid (e.g., Botox®) into the bladder;

forming cavitations in the fluid within the bladder; and
draining the bladder.
Method B in which:
deploying a catheter for ultrasonic-driven treatment of a bladder wall in a bladder;
supplying therapeutic fluid (e.g., Botox®) into the bladder;
forming cavitations in the fluid within the bladder for a predetermined period of time followed by
leaving the therapeutic fluid in the bladder for a predetermined period of time; and
draining the bladder.
Method C in which:
deploying a catheter for ultrasonic-driven treatment of a bladder wall in a bladder;
supplying the bladder with gaseous fluid;
forming cavitations in the gaseous fluid;
draining the gaseous fluid; and
supplying the bladder with therapeutic fluid.
Method D in which:
deploying a catheter for ultrasonic-driven treatment of a bladder wall in a bladder;
supplying the bladder with gaseous therapeutic fluid;
forming cavitation in the gaseous fluid for a predetermined period of time;
followed by
draining the bladder.

Figure 8A:
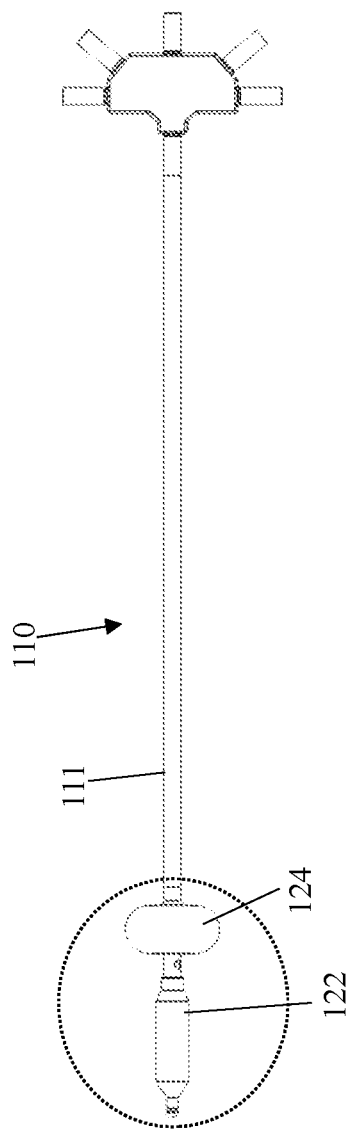
FIGS. 8A and 8B, collectively referred to as FIG. 8, are a plan view and a perspective enlarged view of encircled area in FIG. 8A, simplified illustration of a catheter for ultrasonic-driven bladder therapeutic agent delivery in accordance with some embodiments of the invention.
Figure 8B:
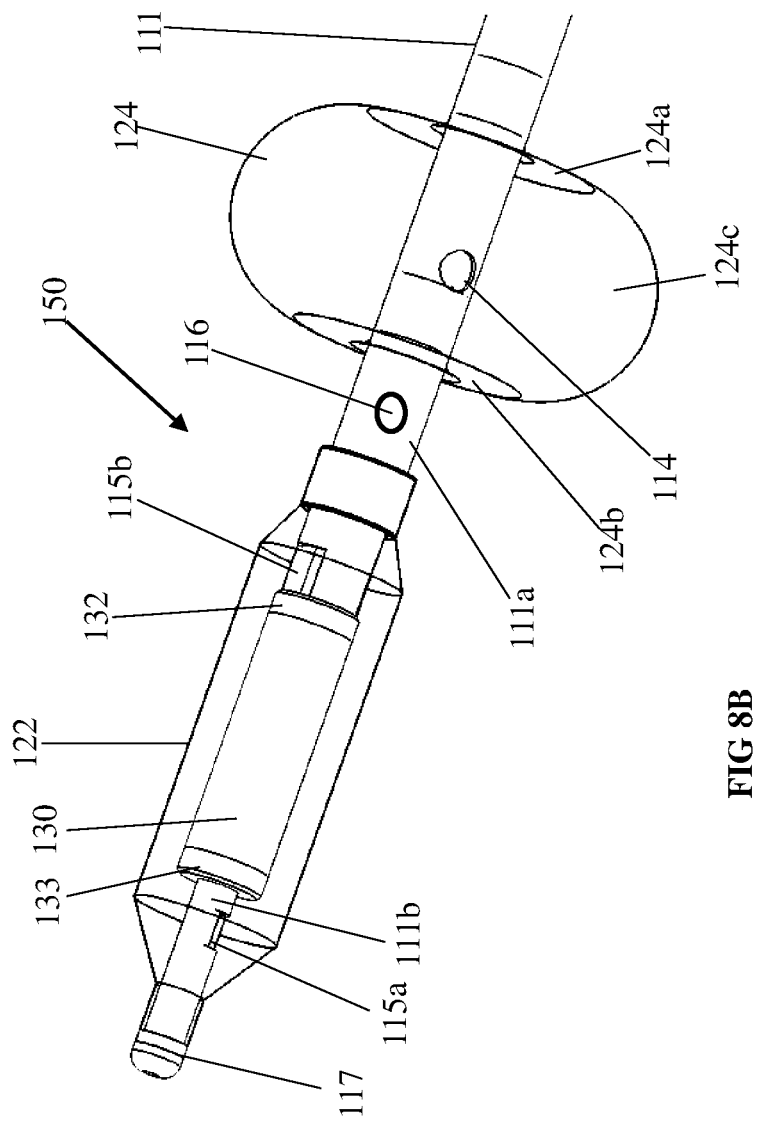

Reference is now made to FIGS. 8A and 8B, collectively referred to as FIG. 8, which are a side view and perspective view simplified illustration of a catheter for ultrasonic-driven bladder therapeutic agent delivery in accordance with some embodiments of the invention. As shown in FIG. 8, a catheter 110 comprises a tube 111, a proximal balloon 124 mounted on the tube 111, and an expandable transducer sleeve 122. Turning to the enlarged view B in FIG. 8, in some embodiments, a distal portion 111b of tube 111 comprises a smaller diameter than the diameter of proximal portion 111a of tube 111. In some embodiments, as shown in view B in FIG. 8, portion 111b comprises the distal tip 117. In some embodiments, portion 111b is connected to tube 111 under a proximal edge of transducer 130. In some embodiments, transducer 130 is mounted on portion 111b of tube 111 so that an external surface of transducer 130 is positioned flush with proximal portion 111a of tube 111. In some embodiments, portion 111b comprises a narrow tube portion inserted within tube 111.

In some embodiments, a transducer 130 is mounted on tube 111 portion 111b between the proximal expandable portion 124 and a distal end 117 of the tube. In some embodiments, the transducer sleeve 122 accommodates and encapsulates the transducer 130 and enables a flow of fluid at the internal volume defined by the walls of transducer sleeve 122. In some embodiments, the tube 111 comprises one or more therapeutic fluid port(s) 116 at a proximal portion 111a of the tube 111, which is free of the expandable portions 122 and 124 and is exposed to the bladder volume.

In some embodiments, proximal balloon 124 is expandable from a collapsed state to an expanded state. In some embodiments, the expanded state is defined as the maximal inelastic expansion of the balloon. In some embodiments, the expanded state of the balloon is defined as a maximal elastic expansion wherein the balloon is elastic. The tube 111 comprises one or more fluid ports 114, 115a and 115b, configured to supply fluid to or remove fluid from at least one of the expandable portions 122 and 124. Expandable portions 122 and 124 are expandable by supplying fluid under positive pressure through at least one of the fluid ports 114, 115a and 115b. In some embodiments, the tube 111 comprises one or more fluid supply channels (not shown), either inside the tube 111 and/or along an outer surface of the tube. In some embodiments, a fluid flow is generated within a lumen defined by walls of transducer sleeve 122 by providing fluid via one of the fluid ports, e.g. port 115a, and removing fluid via another fluid port, e.g. port 115b. In some embodiments, fluid supply port, e.g. port 115a and fluid removal port, e.g. port 115b are disposed on diametrically opposed surfaces of catheter 110. In some embodiments, fluid supply port, e.g. port 115a is located on tube 111 portion 111b whereas the fluid removal port, e.g. port 115b is disposed on tube 111. In some embodiments, fluid supply port, e.g. port 115a and fluid removal port, e.g. port 115b are disposed on opposite sides of transducer 130. In some embodiments, fluid supply port, e.g. port 115a, and fluid removal port, e.g. port 115b, are circumferentially rotated in respect to each other.

In some embodiments, the fluid inputted into the balloon comprises an acoustic fluid. The acoustic fluid maintains a fixed distance between the surface of transducer 130 and transducer sleeve 122. In some embodiments, the acoustic fluid assists in cooling the enclosed transducers 130, for example by heat convection.

In some embodiments, cooling of the transducers helps in their operating in desired parameters for a longer treatment duration, thus, avoiding overheating the tissues while providing an effective treatment. In some embodiments, and as described in greater detail elsewhere herein, removing heat from the transducers prevents overheating of the bladder tissue, which permits an increase in the range of the operational parameters, such as, for example, longer treatment time and/or an increase in transducer frequency.

Figure 9:
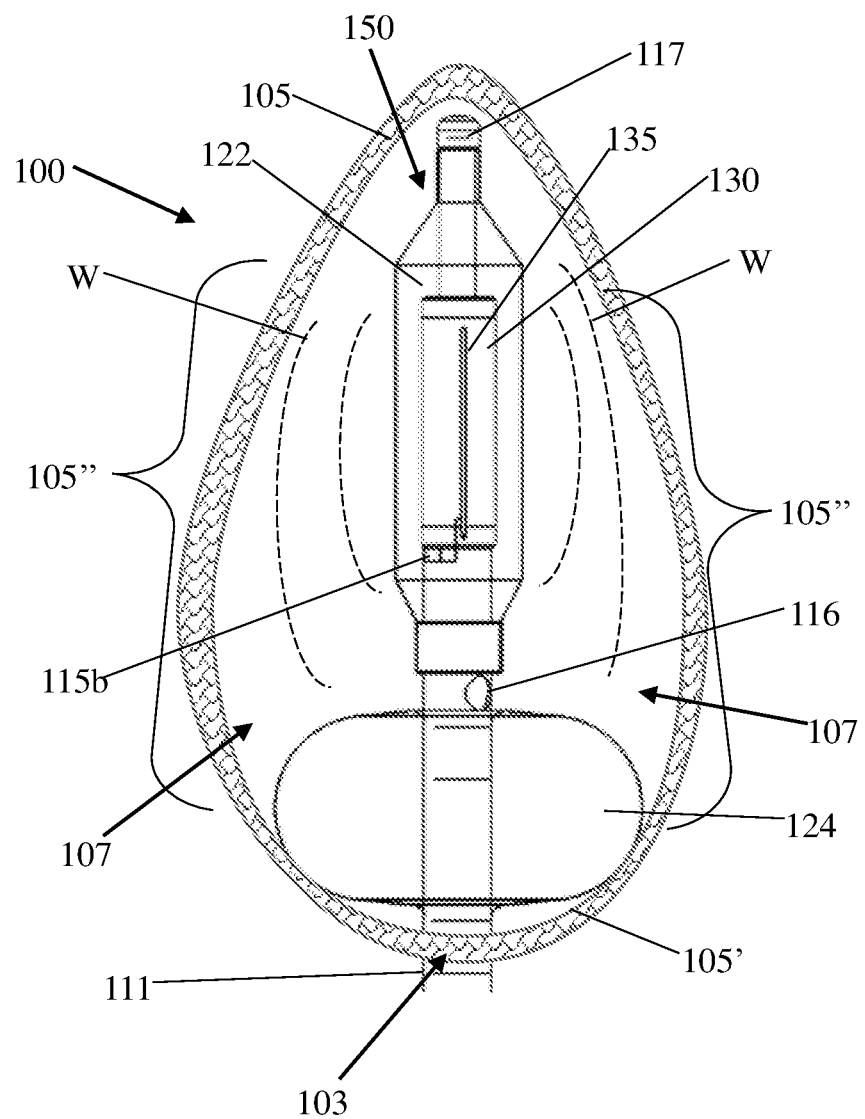
FIG. 9 is a side view simplified illustration of a catheter for ultrasonic-driven bladder therapeutic agent delivery in accordance with some embodiments of the invention.

In some embodiments, e.g., in treatment of the urinary bladder, the procedure is carried out when the bladder is positioned vertically or close to vertically wherein the trigone is lowest portion of the urinary bladder. As shown in the exemplary embodiment depicted in FIG. 9, which is a side view simplified illustration of implementation of an ultrasonic-driven bladder therapeutic agent delivery inside a bladder in accordance with some embodiments of the invention, the proximal balloon 124, at an expanded state, engages the proximal surface of the bladder at the trigone area. The proximal balloon 124 occupies a volume of the bladder 100, thereby forming a treatment volume 107. Balloon 124 at an expanded state blocks drainage of fluid from volume 107 via the balloon wall which is urged against the bladder wall 105. In some embodiments, balloon 124 is urged against and seals the proximal surface (trigone area) of the bladder 105', for example by static forces, such as gravity or fluid pressure. Thereby, the therapeutic fluid remains within volume 107 during the treatment, while the proximal surface (trigone area) of the bladder 105' located distally to proximal balloon 124 remains protected from exposure to the therapeutic fluid and the acoustic energy. In some embodiment of the invention, balloon 124 serves as a catheter base and fixes the position and orientation of the tube 111 in respect to the bladder as well as the elements mounted on the tube within the bladder 100.

Figure 10:
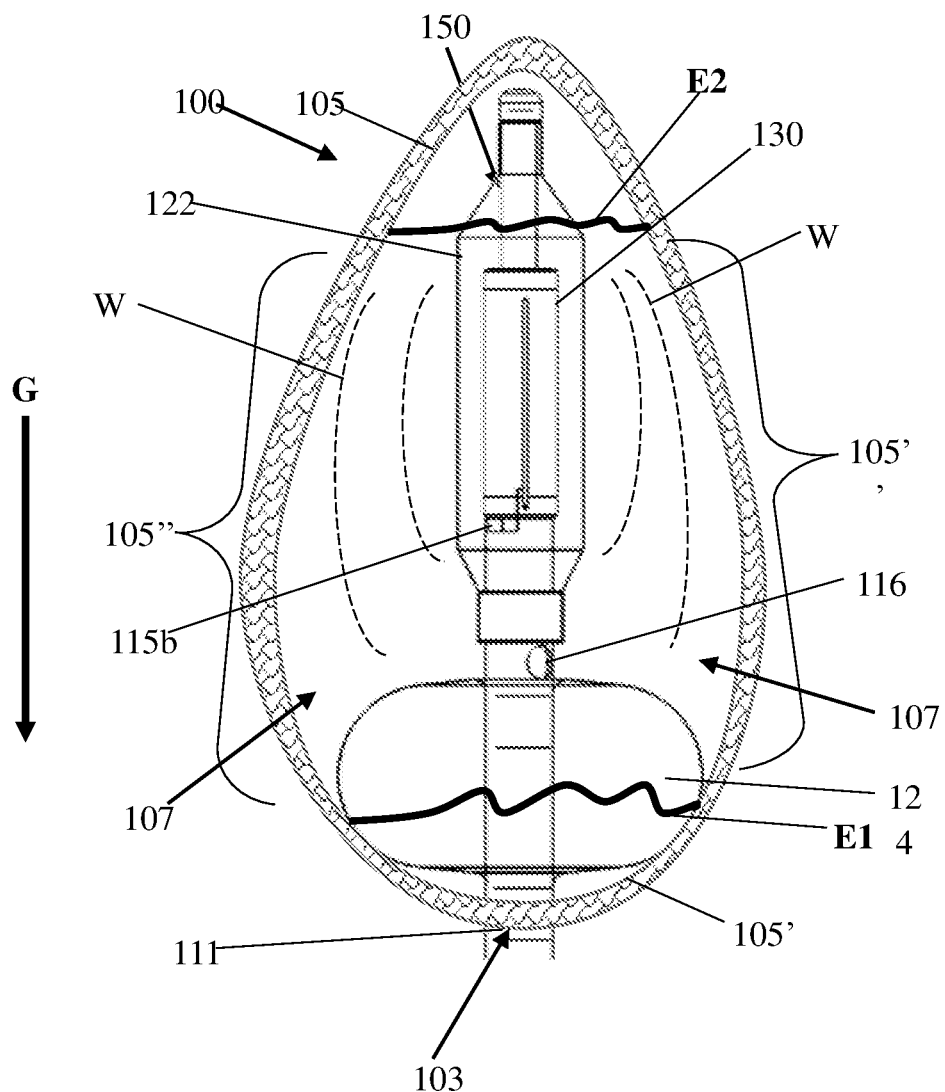
FIG. 10 is a side view simplified illustration of a catheter for ultrasonic-driven bladder therapeutic agent delivery in accordance with some embodiments of the invention.

When a treatment is not required on a distal region or other regions of the bladder, therapeutic fluid can be provided into the bladder in an amount which will fill only a portion of the bladder. During treatment, due to gravitation, the level of fluid will be lower than pre-determined surfaces, so will not be treated by the therapeutic fluid and acoustic energy. As shown in FIG. 10, which is a side view simplified illustration of implementation of an ultrasonic-driven bladder therapeutic agent delivery inside a bladder in accordance with some embodiments of the invention, therapeutic fluid partially fills volume 107 of the bladder 100. Since the bladder 100 is oriented vertically, the direction of gravitation indicated by an arrow (G), the therapeutic fluid remains in between levels E1 and E2. During the treatment, only a portion of the bladder wall which is located distally (above) to proximal balloon 124 in region 105" and within volume 107 will receive the therapeutic fluid and acoustic energy.

In some embodiments, the regions of the bladder wall affected by the treatment are defined by the following dimensions of elements of the catheter 100 such as, for example: the cross section of the proximal balloon 124, the distance between port 116 and face 124b, and the distance between port 116 and the transducer sleeve 122.

The transducer sleeve 122 isolates the transducer 130 from the therapeutic agent and prevents cavitation bubbles from forming near or on the transducer surface. Thereby, the transducer can be disposed farther from the bladder internal wall than in the absence of a transducer sleeve 122. This allows distribution of cavitation bubbles within treatment volume 107, to invoke cavitation on the bladder wall, thus increasing the efficacy of energy emitted towards the bladder wall by the transducers. Some parameters that determine the expanded geometrical shape of the transducer sleeve 122 can be: size and number of the transducers 130 it encloses, flow characteristic of the fluid within its internal volume, desired volume of the bladder extraneous to the transducer sleeve, etc. The transducer sleeve 122 can be characterized to be inelastic having a fixed expanded length, to be rigid or to comprise a stiffening element, and in some embodiments the sleeve can be pressurized to higher pressure than other expandable portions.

Figure 11:
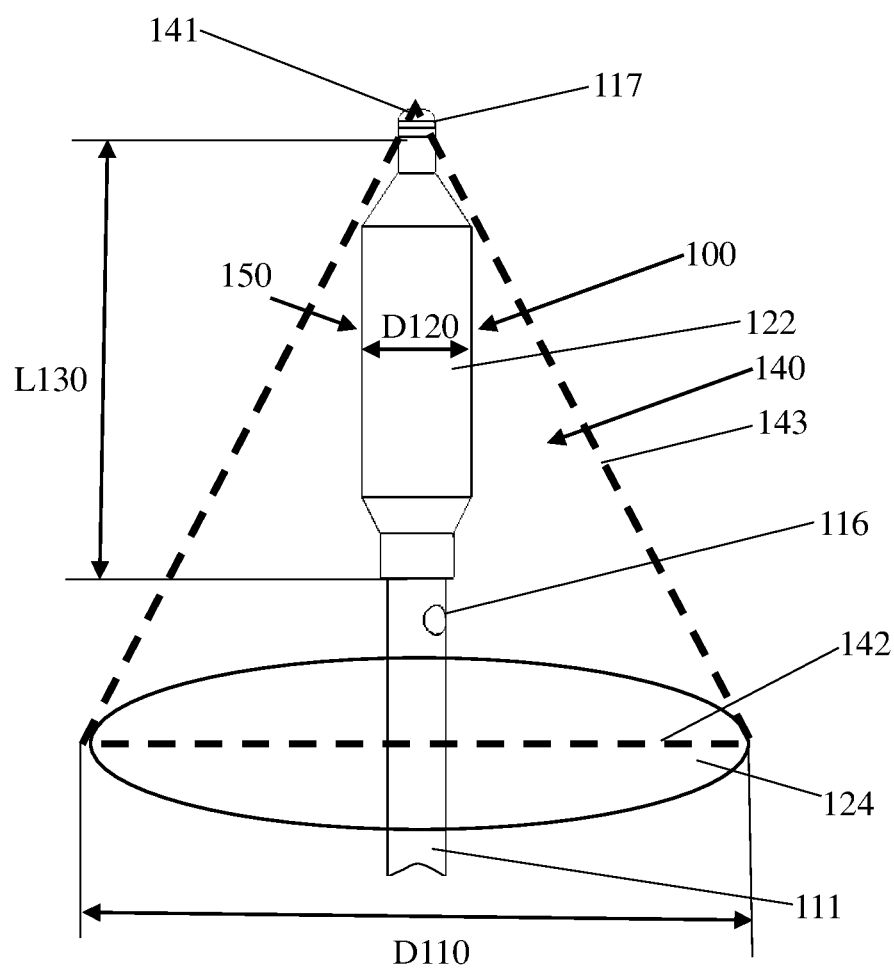
FIG. 11 is a side view simplified illustration of a catheter for ultrasonic-driven bladder therapeutic agent delivery in accordance with some embodiments of the invention.

Turning to FIG. 11, which is a side view simplified illustration of a catheter for ultrasonic-driven bladder therapeutic agent delivery in accordance with some embodiments of the invention. As shown in the exemplary embodiment depicted in FIG. 11, during implementation, the geometry of the catheter 150 protects the wall of the bladder from collapsing onto transducer sleeve 122. As shown in FIG. 11, a bladder wall tends to conform to the geometry of the catheter 10 forming a cone 140 depicted in FIG. 11 by a phantom-line triangle 143. In some embodiments, tip 117 of catheter 150 forms an apex 141 of cone 140 and a base 142 of cone 140 is formed at the maximal cross-sectional area of the proximal balloon 124 at an inflated state. In this configuration, the wall of the bladder is prevented from collapsing onto and contacting transducer sleeve 122 at an inflated state. This constraint can be driven for example by a requirement to maintain a distance between the transducer sleeve walls and the enclosed transducer e.g. in case the bladder surface collapses and engages the sleeve 122, to avoid bending of the sleeve, etc. In some embodiments a diameter D110 of proximal balloon 124 is between 20 mm and 50 mm at an expanded state. In some embodiments, a diameter D110 of proximal balloon 124 is between 30 mm and 38 mm at an expanded state. In some embodiments, a diameter D120 of a transducer sleeve 122 is between 5 mm and 20 mm. In some embodiments, a diameter D120 of a transducer sleeve 122 is between 8 mm and 17 mm. In some embodiments, a diameter D120 of a transducer sleeve 122 is between 12 mm and 14 mm. In some embodiments a length L130 of the transducer sleeve is between 5 and 50 mm at an expanded state. In some embodiments a length L130 of the transducer sleeve is between 15 and 40 mm at an expanded state.

In some embodiments, catheter 150 can comprise two distinct balloons such as shown, for example, in FIGS. 8 to 12. In some embodiments, different pressures or different pressuring fluids can be used for the expansion of the proximal balloon 124 and the transducer sleeve 122 portions. In some embodiments, only portions of the wall of balloon 124 are elastically inflatable, while other portions are inelastic.

In some embodiments, a method for deployment of the ultrasonic-driven catheter according to some embodiments of the invention includes:
- Inserting catheter 110 into bladder 100 through urethra 103 until the distal end 117 engages the bladder distal (opposing the trigone) internal surface 105;
- Expanding balloon 124 and the transducer sleeve 122 to a pre-determined pressure or volume by a pressurized acoustic fluid and maintaining all expanded portions at an expanded state;
- Draining the bladder 100 through therapeutic fluid port(s) 116;
- Washing the bladder by inserting saline and draining the saline through port(s) 116;
- Mixing therapeutic fluid with gassed liquid as described elsewhere herein (this step can be optional or performed any time prior or during the deployment of the catheter); and
- Providing a therapeutic fluid through therapeutic fluid port(s) 116.

In some embodiments, a method for treatment of a bladder wall using an ultrasonic-driven catheter according to some embodiments of the invention includes:
- Fixing catheter 110 within bladder 100 by ensuring expanded balloon 124 engages the proximal wall (trigone area) 105' of the bladder;
- According to some embodiments of the invention, circulating the acoustic fluid within the transducer portion 122 by supplying fluid via a first fluid port 115a and removing acoustic fluid via a second fluid port 115b; and
- Activating the transducer 130.

In some embodiments, the ultrasonic-driven treatment performed by the catheter 110 inserted within a bladder 100 is terminated by the following method, according to some embodiments of the invention:
- Inactivating the operation of transducer 130;
- Removing therapeutic fluid via therapeutic fluid ports 116;
- Inserting saline on bladder surface 105 through ports 116 (e.g. to clean the bladder).
- Collapsing expanded portions 124, 122 by releasing or evacuating the acoustic fluid via the acoustic fluid ports 114, 115a and 115b; and
- Withdrawing catheter 110 out of the bladder 100 through urethra 103.

In accordance to some embodiments of the invention, the deployment of the catheter for ultrasonic-driven treatment of a bladder wall and treatment is carried out within the bladder, by the following method:
- Inserting catheter 110 into bladder 100 through a urethra 103;
- Expanding balloon 124 and the transducer sleeve 122, to a pre-determine pressure or volume by a pressurized acoustic fluid (e.g. 20-40 cc of fluid) and keeping expanded balloon 124 and transducer sleeve 122 at an expanded state;
- Draining the bladder of fluid through therapeutic fluid port(s) 116;

Supplying saline through therapeutic fluid port(s) 116;

Supplying a gassed liquid as described elsewhere herein through bladder therapeutic fluid port(s) 116;

Activating the transducer 130;

Inactivating transducer 130;

Draining the bladder 100 of gassed fluid through therapeutic fluid port(s) 116;

Supplying a therapeutic fluid (e.g. 20-40 cc) through therapeutic fluid port(s) 116.

In some embodiments of the catheter for ultrasound-driven treatment of a bladder, at least one of the expandable portions at an expanded state is shaped as at least one of a sphere, a spheroid or a toroid. In some embodiments, at least one of the expandable portions at an expanded state comprises a C-shaped cross-section. In some embodiments, at least one of the expandable portions at an expanded state comprises an umbrella configuration.

Figure 12:
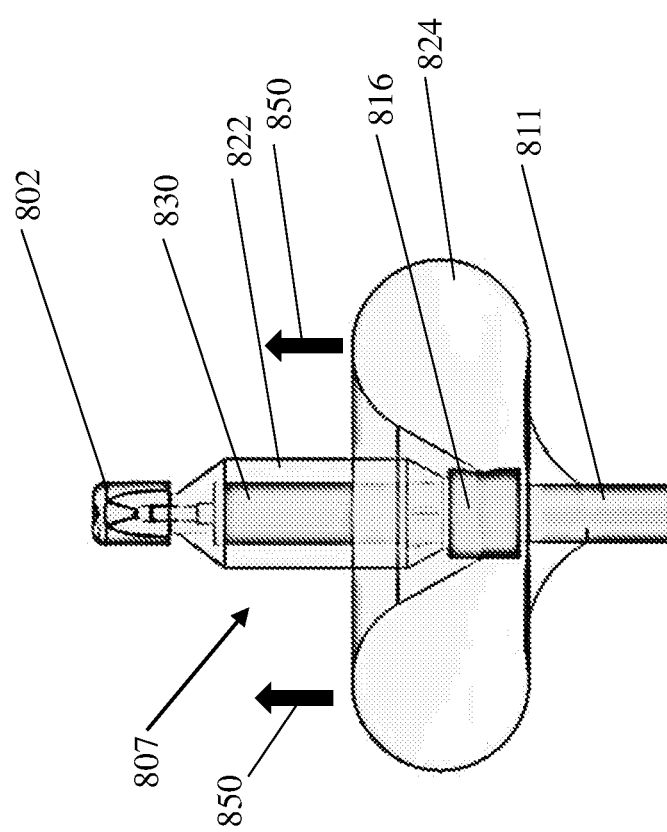
FIG. 12 is a side view simplified illustration of a catheter for ultrasonic-driven bladder therapeutic agent delivery in accordance with some embodiments of the invention.

For example, FIG. 12 shows an embodiment in which the expandable portion 824 is toroidal in geometry. In some embodiments, catheter 811 comprises a therapeutic fluid port 816 between a transducer sleeve 822 and the expandable portion 824. In the exemplary embodiment shown in FIG. 12, toroidal expandable portion 824 when inflated, expands distally, along catheter tube 811 towards tip 802 as indicated by arrows 850 and directing any therapeutic fluid supplied via therapeutic fluid port 816 into treatment volume 807 to surround transducer 830 thus increasing treatment efficacy.

A potential advantage in this configuration is in that the treatment area is more limited and therefore defined more accurately and that a lower amount of therapeutic fluid is required to treat a given area of bladder wall limiting waste of therapeutic fluid.

Shaping of any of the balloons can done by: molding, differential thickness, varying materials, integral elements, etc. Another method for shaping any of the balloon portions can be by limiting its expansion by external elements, such as a sleeve or a net.

In some embodiments, the catheter for ultrasound-driven treatment of a bladder is configured to comprise energy supply conduits for the ultrasound transducer 30/130/830. Additionally, in some embodiments, the catheter for ultrasound-driven treatment of a bladder comprises one or more thermocouples disposed within one or more of the expandable portions. In some embodiments, the thermocouple is configured to measure fluid temperature within the treatment volume. In some embodiments, one or more thermocouples are configured to measure temperature of the bladder wall tissue to prevent overheating of the wall of the bladder. In some embodiments, one or more of the thermocouples are coupled to the bladder wall. In some embodiments, the thermocouple is configured to measure fluid temperature within one or more of the expandable portions and/or the transducer sleeve. In some embodiments, the thermocouple is configured to measure temperature over the surface of the transducer. In some embodiments, the catheter for ultrasound-driven treatment of a bladder comprises one or more pressure sensors within at least one of the expandable portions configured to monitor fluid pressure within the expandable portion. In the exemplary embodiments illustrated in FIGS. 1 and 4, the transducers 30/130 are cylindrical. However, in other embodiments, the transducer can be flat. In some embodiments, transducers 30/130 are mounted on the tube 11/111 by spacers 32/132 and 33/133. Fixation of the transducer at a pre-determined location on the tube provides predictable and repeatable energy parameters.

In some embodiments, the spacers 32/132 and 33/133 are configured to support the transducers elevated from tube 11/111, so to form a gap between the transducer and the tube 11/111. In some embodiments the gap is in the range between 0.05 mm and 4 mm. In some embodiments the gap is in the range between 0.1 mm and 2.5 mm. In some embodiments, the gap is filled by acoustic fluid flowing within the enclosing transducer sleeve 22/122, which can result in cooling of the transducer. In some embodiments, the gap is filled by acoustic fluid which flows within the transducer sleeve 22/122, thereby transferring heat form the transducer.

In some embodiments, the one or more of the spacers 32/33/132/133 is mounted on the tube 11/111. In some embodiments, the transducer 30/130 is mounted on one or more of the spacers 32/33/132/133. In some embodiments, a transducer 30/130 is positioned onto one spacer 32/33/132/133. In some embodiments, the transducer 30/130 is positioned on a plurality of spacers 32/33/132/133. In some embodiments, the length of the spacer 32/33/132/133 is larger than the outermost radius of the spacer 32/33/132/133. In some embodiments, the length of the spacer is at least 50% of the length of the transducer 30/130. In some embodiments, the length of the spacer 32/33/132/133 is up to 30% of the length of the transducer 30/130.

In some embodiments, the spacer 32/33/132/133 adds concentricity, electrical protection, and mechanical scaffold to the catheter for ultrasonic-driven bladder drug delivery. In some embodiments, distancing the transducer from the catheter and/or tube provides electrical insulation by having an isolation medium (e.g., air) between the transducer and the catheter.

Turning to FIGS. 13 and 14, which are simplified illustrations of side views of a catheter for ultrasonic-driven bladder drug delivery, in accordance with some embodiments of the present disclosure. As shown in FIGS. 13 and 14, normally open stents, e.g. expandable stents 224, 324, 326, replaces at least some of expandable portions disclosed in the preceding embodiments, such as 24, 26, 124, can be replaced by normally open stents, e.g. expandable stents 224, 324, 326. Each of the stents 224, 324, 326 are configured as normally open and remains enclosed within a stent sleeve (not shown) prior to inserting the catheter 210/310 into a bladder. The stents are configured to open upon exposing out of the stent sleeve and to engage the bladder wall. Any of the stents can have a fluid sealing surface to block fluid within a bladder cavity volume defined within the bladder on one side of the sealing surface to flow into a bladder cavity volume defined on an opposite side of the stent sealing surface.

In the embodiments illustrated in FIGS. 1 and 8, the transducers are fixed to the tube by spacers (e.g. 32/132 and 33/133). The fixation of the transducer at a pre-determined location and centralized around the tube, helps providing predictable and repeatable energy parameters. The spacers support the transducers, such that a gap is defined between the transducer and the tube. In some embodiments, the gap is in the range of 0.05 to 4 mm. In some embodiments, the gap is in the range of 0.1 to 2.5 mm. In some embodiments, the gap is filled by an acoustic fluid which flows within the enclosing transducer sleeve 22/122/222/322/822, thereby cooling the transducer.

In some embodiments, at least one of stents 224, 324, 326 is replaceable by a balloon. In some embodiments, the catheter for ultrasonic-driven bladder drug delivery comprises at least one balloon, at least one stent, or any combination thereof.

The following are some examples of treatment parameters that enable an effective and safe treatment, according to some embodiments of the invention:

In some embodiments, the ultrasound transducer is between 100-400 Khz. In some embodiments, the ultrasound transducer is between 125-350 Khz. In some embodiments, the ultrasound transducer is between 150-300 Khz.

In some embodiments, the ultrasound transducer duty cycle is between 5-50%. In some embodiments, the ultrasound transducer duty cycle is between 7-45%. In some embodiments, the ultrasound transducer duty cycle is between 10-40%.

In some embodiments, the ultrasound Isppa intensity is between 5-60 W/cm2. In some embodiments, the ultrasound Isppa intensity is between 8-55 W/cm2. In some embodiments, the ultrasound Isppa intensity is between 10-50 W/cm2.

The bladder distance from the ultrasound transducer ranges between 1-30 mm

In some embodiments, the total treatment time in which the transducer is in use ranges between 5-30 minutes. In some embodiments, the total treatment time in which the transducer is in use ranges between 10-25 minutes. In some embodiments, the total treatment time in which the transducer is in use ranges between 15-20 minutes.

In some embodiments, the acoustic fluid pressure ranges between 0.3 Mpa to 2 Mpa. In some embodiments, the acoustic fluid pressure ranges between 0.5 Mpa to 1 MPa.

In some embodiments, 3-40 mL of fluid fill up the volume of the transducer sleeve. In some embodiments, 5-20 mL of fluid fill up the volume of the transducer sleeve. In some embodiments, 10-14 mL of fluid fill up the volume of the transducer sleeve.

In some embodiments, 3-100 mL of fluid fill up the volume of at least one expandable portion 24/26/124/824. In some embodiments, 10-70 mL of fluid fill up the volume of at least one expandable portion 24/26/124/824. In some embodiments, 30-55 mL of fluid fill up the volume of at least one expandable portion 24/26/124/824.

In some embodiments, 5-300 mL of fluid is streamed into the bladder volume. In some embodiments, 15-100 mL of fluid is streamed into the bladder volume. In some embodiments, 25-50 mL of fluid is streamed into the bladder volume.

Gas bubbles in liquid serve as nucleation seeds for the generation of cavitation. Therefore, increasing the amount of gas bubbles in the therapeutic fluid increases the efficiency of the ultrasound treatment.

Additionally, ultrasound transducers introduced into the bladder are commonly limited in the level of energy they can emit. Additionally, the fluid medium partially blocks and/or slows down ultrasound waves traveling from the transducer towards the bladder wall, thereby exposing the bladder wall to energy which may be insufficient for driving the treatment agent onto the tissue. Hence, to achieve efficacious treatment of a bladder wall, the ultrasound transducer needs to be activated in close proximity to the bladder wall, which increases the risk of damage to the wall tissue due to exposure to excessive heat generated from the transducer.

Introduction of nucleation seeds, such as solid particles, semi-solids, micro-bubbles, and the like, in the therapeutic fluid distributes gas bubbles throughout the fluid. The gas bubbles closer to the transducer absorb a portion of the ultrasound radiation by forming cavitation, however the presence of gas bubbles throughout the treatment volume and especially in proximity to the bladder wall enables their activation (i.e., production of cavitation) even by the low energy ultrasound waves that would be ineffective in the absence of the nucleation seeds. Dispersing of the cavitation in the therapeutic fluid allows cavitation throughout the therapeutic fluid and not only in the layer encountered by ultrasound emitted waves in the immediate surroundings of the transducer sleeve.

The presence of these bubbles therefore reduces the energy threshold required for cavitation generation. This allows using less acoustic energy, thus making the treatment safer to tissues. In some embodiments, increasing the amount of cavitation bubbles within the therapeutic fluid liquid is prepared by adding gassed sterile liquid, such as saline within the therapeutic agent.

In some embodiments of the present invention there is provided a method for increasing the amount of cavitation bubbles within the therapeutic fluid liquid including:
- pressurizing a sterile liquid with a gas to generate a gassed liquid;
- maintaining the gassed liquid compressed for a predetermined duration;
- preparing a therapeutic fluid by releasing a therapeutic agent (formed as a powder or a liquid) into the gassed liquid.

For example, in some embodiments, the gas is at least one of air, helium, nitrogen, oxygen, or any combination thereof. In some embodiments, the pressurizing of a sterile liquid with a gas is at a pressure of 8 to 30 atmospheres. In some embodiments, the predetermined duration is between 0.5-2 hours. In some embodiments, the predetermined duration is 1 hour.

When adding the gassed liquid into the therapeutic fluid, the equilibrium of gases is swayed toward the therapeutic agent, thereby increasing the gas content therein. When it decompresses (as pressure is immediately released) within the therapeutic agent, the equilibrium of gases is swayed back towards the surrounding atmosphere and the excess gas is released in the form of small bubbles. These small bubbles serve as cavitation nucleation sites during the treatment.

In some embodiments, the therapeutic fluid is mixed into the gassed fluid. in some embodiments, the gassed fluid is mixed into the therapeutic fluid. in some embodiments, the gassed fluid is a diluent for the therapeutic fluid.

Example 1

The following experiment was done to determine the efficacy of treatments using catheter for ultrasonic-driven treatment of a bladder compared to untreated tissue and gold standard 100 units Botox® intravesical injections.

Reference is made to FIG. 15, which is an exemplary chart of parameters of implementation of a catheter for ultrasonic-driven treatment of a bladder, in accordance with some embodiments of the invention. the following experiment was tested on 8 pigs.

In the present example, the ultrasonic-driven treatment of the bladder by implementation of the catheter for ultrasonic-driven treatment of a bladder begins by application of local anesthesia to the bladder 1. Next, the catheter 10 is inserted at step 1400 into bladder 1 through a urethra 3 and the expandable portions 24, 26, and transducer sleeve 22 are expanded at step 1420 by inflating 10-15 mL. In the present example, the bladder 1 is washed twice with saline by supplying at step 1440 saline and then draining the bladder 1 at step 1430 through therapeutic fluid port(s) 17.

Next, 30 mL of therapeutic fluid is then instilled to the bladder, and the expandable portions 24, 26, and transducer sleeve 22 are fully inflated inside the bladder to 35 mL. A pump is started to circulate acoustic fluid within the expandable portions 24, 26, and transducer sleeve 22. The transducer is switched on at a frequency of 200 kHz for 15 minutes, and turned off, as depicted by FIG. 15. The duty cycle of the transduce is 15%. Lastly, the therapeutic fluid is incubated within the bladder post-treatment for 10 minutes, as depicted by FIG. 15.

In the present example, the therapeutic is botulinum toxin A (Botox®) solution in saline. The dose of the toxin is 100-200 units. In this example, the saline is normal sterile saline. In some embodiments, and in this example, the fluid is not gassed.

Additionally, 3 pigs were treated with the gold standard 100 units Botox® intravesical injections.

Pathological reports of the bladders, kidneys, urethras, ureters, and other organs were taken. Additionally, the efficacy of the treatments of catheter for ultrasonic-driven treatment of a bladder was compared to the gold standard 100 units Botox® intravesical injections and to a control group of pigs which did not received any treatment was measured by measuring the contractility of the detrusor muscle after each treatment.

Figure 16:
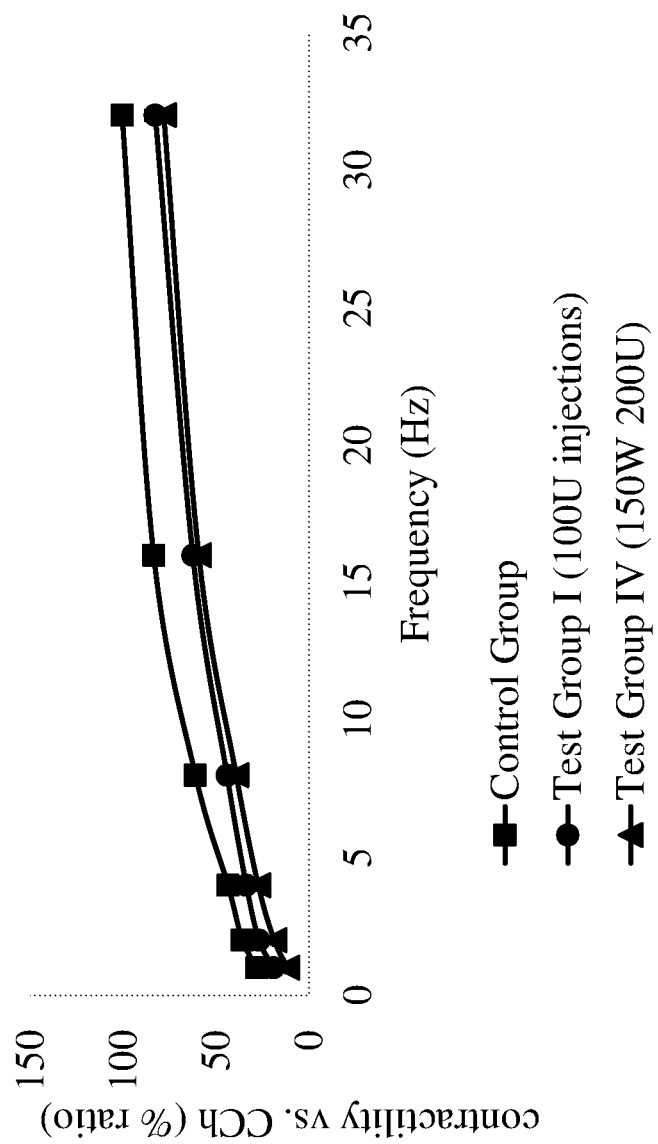
FIG. 16 is a graph of the contractility of the detrusor muscle after each treatment: treatments using catheter for ultrasonic-driven treatment of a bladder compared to untreated tissue, and gold standard 100 units Botox® intravesical injections.

Reference is made to FIG. 16, which is a graph of the contractility of the detrusor muscle after each treatment: treatments using catheter for ultrasonic-driven treatment of a bladder compared to untreated tissue, and gold standard 100 units Botox® intravesical injections. The contractility of the detrusor muscle after each treatment as shown by the y-axis is a percent ratio of the contractility after a treatment in relation to the contractility of the detrusor muscle after receiving carbachol (CCh). The contractility vs. CCh ratio depicts how much each detrusor muscle contracted in relation to a maximal contraction achieved by the CCh treatment.

In the graph of FIG. 16, 100% contractility vs. CCh is consistent with no Botox® activity whereas lower percent of muscle activity is correlated with Botox® administration. It is shown that shows that both the treatments using catheter for ultrasonic-driven treatment and the gold standard 100 units Botox® intravesical injections achieved better results than the control group which was untreated, however, the efficacy of treatments using catheter for ultrasonic-driven treatment is at least the same or higher than the gold standard intravesical injections treatment.

For example, at a frequency of 8 Hz, the bladders which received treatment using the catheter had a contractility vs. CCh ratio of about 39%, whereas the bladders which received the intravesical injections had a contractility vs. CCh ratio of about 44%, and the control group was at about 61%.

At a frequency of 32 Hz, the bladders which received treatment using the catheter had a contractility vs. CCh ratio of about 78%, whereas the bladders which received the intravesical injections had a contractility vs. CCh ratio of about 82%, and the control group was at 100%.

Example 2

The following experiment was done to determine the efficacy of treatments using catheter for ultrasonic-driven treatment of an Overactive bladder (OAB) in human patients. The parameters of implementation for the catheter for ultrasonic-driven treatment correspond to the table depicted by FIG. 16 and the parameters of the treatment in pigs shown in Example 1. Ten humans were treated and observed for 14 days post procedure.

Results of the treatment in humans' bladders using the catheter for ultrasonic-driven treatment showed no adverse events, serious or non-serious. Additionally, specific data of bladder function was obtained from two patients pre and post procedure.

Patients suffering from an overactive bladder experience sudden urges to urinate and frequent urinations during both day and night, caused by involuntary contractions by the detrusor muscle.

Reference is made to FIG. 17, which is a table of efficacy data from two human patients comparing pre-procedure bladder function to 14 days post procedure bladder function. As shown in FIG. 17, the average volume of each micturation increased by 22% and 27% for patients 3002 and 3004, respectively. Increase in the volume of each micturation is indicative of more urine filling up the bladder of the patient before urination. Additionally, the average number of nocturnal urinations has decreased by 60% and 10% for patients 3002 and 3004, respectively, which corresponds to the increase in volume of each micturation. An increase in the volume of each micturation decreases the number of times a patient needs to urinate.

As shown in FIG. 17, the average number of urinary incontinence for patient 3004 decreased by 62.5%. patient 3002 experienced no change in the average number of urinary incontinence. The decrease of number of urinary incontinence shows the efficacy of the treatment using the catheter for ultrasonic-driven treatment in human patients suffering from OAB.

Lastly, post procedure OAB-q (14 days post-procedure) were compared to pre-procedure OAB-q of patients 3002 and 3004, showing a decrease of 4.1% and 38.6%, respectively. The decrease of the OAB-q scores indicates an increase in general wellbeing and decrease in severity of symptoms of OAB.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A catheter for ultrasonic-driven bladder therapeutic agent delivery, comprising:
   a tube having (i) one or more expandable portions, expandable via one or more first fluid ports, wherein at least one of said one or more expandable portions is a proximal expandable portion, and (ii) a distal end; and
   at least one inflatable transducer sleeve accommodating at least one ultrasound transducer mounted on said tube between said proximal expandable portion and said distal end,
   wherein said at least one inflatable transducer sleeve comprises degassed acoustic fluid, configured to allow acoustic waves to travel from the at least one ultrasound transducer to the at least one inflatable transducer sleeve without generating cavitation, and wherein said at least one inflatable transducer sleeve is expandable via one or more second fluid ports.

2. A catheter according to claim 1, wherein said proximal expandable portion is configured to be expandable inside a bladder from a contracted state to an expanded state in which said proximal expandable portion is configured to be urged against a wall of the bladder, to form a sealed volume within the bladder between said proximal expandable portion and a trigone area of said bladder.

3. A catheter according to claim 1, wherein a maximal cross-sectional area of the at least one inflatable transducer sleeve at an expanded state thereof is smaller than a maximal cross-sectional area of any one of the one or more expandable portions at least at their greatest circumference.

4. A catheter according to claim 1, wherein at least one of the tube and the at least one ultrasound transducer are concentric with at least one of the one or more expandable portions.

5. A catheter according to claim 1, wherein the tube comprises at least one of the one or more first fluid ports located within a lumen of at least one of the one or more expandable portions.

6. A catheter according to claim 1, wherein the tube comprises at least two of the one or more second fluid ports in fluid communication with a lumen of said at least one inflatable transducer sleeve and wherein fluid flow is maintained between said one or more second fluid ports, and wherein said at least one ultrasound transducer is positioned between said one or more second fluid ports.

7. The catheter according to claim 6, further comprising a thermocouple device configured to monitor fluid temperature within one or more of the one or more expandable portions and/or the at least one inflatable transducer sleeve, and wherein flow of the degassed acoustic fluid is maintained between at least two of the one or more second fluid ports to cool the at least one ultrasound transducer by heat convection.

8. A catheter according to claim 1, wherein the tube comprises at least one therapeutic fluid port along its length that is configured to open to a lumen of the bladder.

9. A catheter according to claim 8, further comprising a blind tip at said distal end, wherein said at least one therapeutic fluid port is positioned along the circumference of the tip.

10. A catheter according to claim 1, wherein the at least one ultrasound transducer is elevated from a surface of the tube so as to define a gap between the at least one ultrasound transducer and the surface of the tube.

11. A catheter according to claim 1, further comprising at least one spacer positioned on said tube and wherein said at least one ultrasound transducer is mounted on said at least one spacer.

12. A catheter according to claim 1, wherein the at least one of the one or more expandable portions is one of: toroidal and spheroid.

13. The catheter of claim 1 further comprising one or more pressure sensors, configured to monitor fluid pressure, and wherein at least one of the one or more expandable portions and the at least one inflatable transducer sleeve are expandable by pressurizing the degassed acoustic fluid to a predetermined pressure.

14. The catheter according to claim 1, wherein the tube comprises a fluid supply port and a fluid removal port in fluid communication with a lumen of said at least one inflatable transducer sleeve, wherein the at least one or more second fluid ports comprise said fluid supply port and said fluid removal port, and wherein said at least one ultrasound transducer is positioned between said fluid supply port and said fluid removal port, and wherein flow of the degassed acoustic fluid is maintained between said fluid supply port and said fluid removal port to cool the at least one ultrasound transducer by heat convection.

15. The catheter according to claim 14, wherein the fluid supply port and fluid removal port are circumferentially rotated in respect to each other.

* * * * *